United States Patent [19]
Chenard et al.

[11] Patent Number: 5,962,457
[45] Date of Patent: Oct. 5, 1999

[54] 2,3 DISUBSTITUTED- (5,6)-HETEROARYLFUSED-PYRIMIDINE-4-ONES

[75] Inventors: Bertrand L. Chenard, Waterford; Willard M. Welch, Jr., Mystic, both of Conn.

[73] Assignee: Pfizer Inc., New York, N.Y.

[21] Appl. No.: 08/855,630

[22] Filed: May 14, 1997

Related U.S. Application Data

[60] Provisional application No. 60/017,737, May 15, 1996.

[51] Int. Cl.$^6$ ...................... C07D 487/02; C07D 491/02; C07D 495/02; A61K 31/38
[52] U.S. Cl. ........................... 514/258; 544/278; 544/280
[58] Field of Search .................................. 544/278, 280; 514/258

[56] References Cited

U.S. PATENT DOCUMENTS

| | | | |
|---|---|---|---|
| 3,558,610 | 1/1971 | Breuer et al. | 260/240 |
| 5,124,331 | 6/1992 | Arita et al. | 514/253 |
| 5,252,584 | 10/1993 | Carling et al. | 514/312 |
| 5,268,378 | 12/1993 | Baker et al. | 514/312 |
| 5,284,957 | 2/1994 | Huff | 548/112 |
| 5,426,106 | 6/1995 | Kulagowski et al. | 514/233.2 |
| 5,475,008 | 12/1995 | Carling et al. | 514/312 |

FOREIGN PATENT DOCUMENTS

| | | |
|---|---|---|
| 769844 | 1/1972 | Belgium . |
| 2131843 | 11/1972 | France . |
| 2114607 | 10/1972 | Germany . |
| 1298603 | 7/1973 | United Kingdom . |
| WO9213535 | 8/1992 | WIPO . |

OTHER PUBLICATIONS

Chem. Abstract 77:5512t, Jul. 1972.
Damasio, Alzheimer's Disease and Related Dementias, Cecil Textbook of Medicine, 20th Edition, vol. 2, pp. 1992–1996, 1996.
Synthesis of Some New 2–Styryl–3–0–Tolyl–4–Quinazolone as compound of Antifungal Activity; J. Inst. Chemists (India); vol. 60, pp. 58; Mar. 1988; (Miss.) Malti Rawat.
Synthesis of Some Quinazolones; Indian J. Pharm. Sci., 1986, 48(5), pp. 133–136; Jun. 1985; Vijai K. Srivastava, et al.
Synthesis of Heterocyclic Compounds Incorporating 4–Aminostilbene; Indian J. of Chem., vol. 24B, pp. 1039–1042; Oct. 1985; Rajendra S. Varma, et al.
Synthesis and Hypotensive Activity of Trisubstituted Quinazolinones; Eur. J. Med. Chem. Chim. Ther., 1985–20, No. 1, pp. 95–96; A. Kumar, et al.
Synthesis and Antiinflammatory Activity of 2–Substituted–Phenethyl–3–Substituted–Phenyl–4(3H)–Quinazolinones; Indian J. of Chem., vol. 23B, pp. 592–594; Jun. 1984; Inder Pal Singh, et al.
Recent Progress in Excitatory Amino Acid Research; Annual Reports in Medicinal Chem.; Chapter 6, pp. 53–64; 1994; James A. Monn, et al.

Neuronal Cell Death and Strategies for Neuroprotection; Annual Reports in Medicinal Chem.; Chapter 2, pp. 13–22; 1994; Christopher F. Bigge, et al.
Substituierte Chinazolinone–(4) als Hypnotica und Antikonvulsiva; pp. 688–701; Von K.–H. Boltze, et al.
Synthesis of Some 4H–3, 1–Benzoxazin–4–Ones and 4–Quinazolones and Their Reaction with Hydrazines; U.A.R. J. Chem., 14, No. 2, pp. 197–205; 1971; A. Sammour, et al.
Anticonvulsant and Monoamine Oxidase Inhibitory Properties of newer Chlorostrylquinazolones; Pharm. Research Communications, vol. 11, No. 7, pp. 623–633; 1979; R. S. Misra, et al.
Synthesis of Some Quinazolone Derivatives Structurally Related to Certain Sedatives, Hypnotics and Anticonvulsant Agents; Pharmazie 34, H. 11, 1979; A. K. El–Ansary, et al.
Correlation between Monoamine Oxidase Inhibitors and Anticonvulsants; J. of the National Medical Assoc., vol. 72, No. 10, pp. 953–955, 1980; Chundradhar Dwivedi, et al.
Synthesis of Some 4–Substituted Phenylmercaptoacetic Acids; Arch. Pharm. (Weinheim) vol. 314, pp. 97–103, 1981; Rajendra S. Varma, et al.
Synthesis of 2–Styryl–3,6,8–Trisubstituted Qinazolin 4(3H) Ones as Anti–Inflammatory Agents; J. Chem. Soc. Pak.; vol. 3, No. 4, pp. 209–213, 1981; V. S. Misra, et al.
Antimicrobial Activity of 2,3–Disubstituted 4 (3H)–Quinazolone Derivatives; Indian Journal of Forestry; vol. 7(2), pp. 151–153, 1984; S. K. Shukla, et al.
Synthesis of Certain 4 (3H) Quinazolinones likely to Possess CNS Depressant and Antimalarial Activities; Egypt J. Pharm. Sci. vol. 29 No. 1–4, pp. 595–604, 1988; U. L. El Sabagh, et al.
Synthesis and Antifungal Activityof 2–(4–aryl–2–pyrazolin–3–yl)–3–aryl–4–(3H)–Quinazolinones; Indian J. Pharm. Sci., vol. 53 (6), pp. 229–232, 1991; A. Malla Reddy, et al.
Pyrido[3,2–d] pyrimidin–4(3H)–ones; pp. 4240–4246; W. J. Irwin, et al.
Synthesis of Some Quinazolone Derivatives Structurally Related to Certain Sedatives, Hypnotics and Anticonvulant Agents; Dept. of Organic Chemistry; Pharmazie 34, H. vol. 11, 1979; A. K. El–Ansary, et al.
Search for New Anthelmintics Part IV Synthesis of Phenoxy Acid–Salts of Piperazine Containing Quinazolone Moiety; Acta Ciencia Indica; vol. XVI, C, 3, 251, pp. 755–763, 1990; S. S. Tiwari, et al.
4–(3H)–Quinazolones Part II: 2–Alkyl or Arylaminomethyl Substituted Cinnamyl–3–p–(N– Phenylthiouredosulfophenyl)– 4–(3H)–Quinazolones; J. Inst. Chemists (India), vol. 63, pp. 66–69, Mar., 1991; V. B. Gaur, et al.

(List continued on next page.)

*Primary Examiner*—Richard L. Raymond
*Assistant Examiner*—Deepak R. Rao
*Attorney, Agent, or Firm*—Peter C. Richardson; Paul H. Ginsburg; Kristina L. Konstas

[57] ABSTRACT

The present invention relates to novel compounds of the formula I, described above, and their pharmaceutically acceptable salts, and pharmaceutical compositions and methods of treating neurodegenerative and CNS-trauma related conditions.

40 Claims, No Drawings

OTHER PUBLICATIONS

Strucuture activity relationships in the development of excitatory amino acid receptor agonists and competitive antagonists; TiPS; vol. 11, pp. 25–33, 1990; Jeff C. Watkins, et al.

The non–NMDA antagonists, NBQX and GYKI 52466, protect against cortical and striatal cell loss following transient global ischaemia in the rat; Institute of Psychiatry; 571, pp. 115–120, 1992; Eliane Le Peillet, et al.

2,3–Dihydroxy–6–nitro–7–sulfamoyl–benzo(F)quinoxaline: A Neuroprotectant for Cerebral Ischemia; Brain Research; vol. 247, pp. 571–574 1990; Malcolm J. Sheardown et al.

Modulation of N–methyl–D–aspartate receptor–mediated increases in cytosolic calcium in cultured rat cerebella granule cells; Brain Research; 552, pp. 13–22, 1991; T. N. Parks, et al.

Delayed AMPA receptor blockade reduces cerebral infarction induced by focal ischemia; NeuroReport; vol. 2, No. 8, pp. 473–476, 1991; Alastair M. Buchan, et al.

(3SR,4aRS,6RS,8aRS)–6–[2–(1H–Tetrazol–5–yl)ethyl] decahydroisoquinoline–3–carboxylic Acid: A structurally Novel, Systemically Active, Competitive AMPA Receptor Antagonist; J. Med. Chem.; pp. 2046–2048, 1993; Paul L. Ornstein, et al.

New Developments in the Molecular Pharmacology of α–Amino–3–hydroxy–5–methyl–4–isoxazole Propionate and Kainate Receptors; Pharmacol. Ther. vol. 70, No. 1, pp. 65–89, 1996; Elizabeth J. Fletcher et al.

ARICEPT® (Donepezil Hydrochloride tablets); US Product Prescribing Information; pp. 1–20, 1998; Pfizer Inc.

2,3 DISUBSTITUTED-(5,6)-HETEROARYLFUSED-PYRIMIDINE-4-ONES

This non-provisional application is based upon and claims priority from Provisional Application No. 60/017,737 filed May 15, 1996.

BACKGROUND OF THE INVENTION

The present invention relates to novel compounds of the formula I, described below, and their pharmaceutically acceptable salts, and pharmaceutical compositions and methods of treating neurodegenerative and CNS-trauma related conditions.

The compounds of the invention are potent AMPA receptor antagonists. AMPA receptors are a subspecies of glutamate receptors, identified by their ability to bind α-amino-3-hydroxy-5-methyl-4-isoxazolepropanoic acid (AMPA), that are implicated as post-synaptic neurotransmitter receptors for excitatory amino acids.

The role of excitatory amino acids, such as glutamic acid and aspartic acid, as the predominant mediators of excitatory synaptic transmission in the central nervous system has been well established. Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). These amino acids function in synaptic transmission primarily through excitatory amino acid receptors. These amino acids also participate in a variety of other physiological processes such as motor control, respiration, cardiovascular regulation, sensory perception, and cognition.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). The second general type is the G-protein or second messenger-linked "metabotropic" excitatory amino acid receptor. This second type, when activated by the agonists quisqualate, ibotenate, or trans-1-aminocyclopentane-1,3-dicarboxylic acid, leads to enhanced phosphoinosoitide hydrolysis in the postsynaptic cell. Both types of receptors appear not only to mediate normal synaptic transmission along excitatory pathways, but also participate in the modification of synaptic connection during development and changes in the efficiency of synaptic transmission throughout life. Schoepp, Bockaert, and Sladeczek. *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

Excitatory amino acid excitotoxicity has been implicated in the pathophysiology of a number of neurological disorders. This excitotoxicity has been implicated in the pathophysiology of acute and chronic neurodegenerative conditions including cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced dementia, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, ocular damage and retinopathy, and idiopathic and drug-induced Parkinson's Disease. Other neurological conditions, that are caused by glutamate dysfunction, require neuromodulation. These other neurological conditions include muscular spasms, migraine headaches, urinary incontinence, psychosis, addiction withdrawal (such as alcoholism and drug addiction including opiate, cocaine and nicotine addiction), opiate tolerance, anxiety, emesis, brain edema, chronic pain, convulsions, retinal neuropathy, tinnitus and tardive dyskinesia. The use of a neuro-protective agent, such as an AMPA receptor antagonist, is believed to be useful in treating these disorders and/or reducing the amount of neurological damage associated with these disorders. The EAA antagonists are also useful as analgesic agents.

Several studies have shown that AMPA receptor antagonists are neuroprotective in focal and global ischemia models. The competitive AMPA receptor antagonist NBQX (2,3-dihydroxy-6-nitro-7-sulfamoylbenzo[f-]quinoxaline) has been reported effective in preventing global and focal ischemic damage. Sheardown et al., *Science*, 247, 571 (1900); Buchan et al., *Neuroreport*, 2, 473 (1991); LePeillet et al., *Brain Research*, 571, 115 (1992). The noncompetitive AMPA receptor antagonists GKYI 52466 has been shown to be an effective neuroprotective agent in rat global ischemia models. LaPeillet et al., *Brain Research*, 571, 115 (1992). These studies strongly suggest that the delayed neuronal degeneration in brain ischemia involves glutamate excitotoxicity mediated at least in part by AMPA receptor activation. Thus, AMPA receptor antagonists may prove useful as neuroprotective agents and improve the neurological outcome of cerebral ischemia in humans.

SUMMARY OF THE INVENTION

The present invention relates to a bicyclic compound of the formula

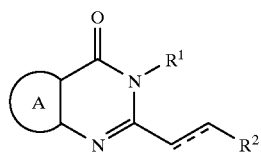

wherein ring A is a fused heteroaromatic ring, wherein said heteroaromatic ring is a 5 or 6 membered heteroaromatic ring, wherein said 6 membered heteroaromatic ring, taken together with the carbon atoms common to both rings of the bicyclic system, has the formula

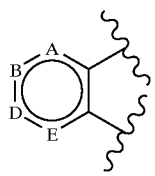

and wherein said 5 membered heteroaromatic ring, taken together with the carbon atoms common to both rings of the bicyclic system, has the formula wherein said ring positions "A", "B", "D" and "E" may be independently selected from carbon or nitrogen;

wherein said ring positions "F", "G" and "J" may be independently selected from carbon, nitrogen, oxygen or sulfur, with the proviso that: i) if more than two of "F", "G" or "J" is a heteroatom then said 5 membered heteroaromatic ring is selected from the group consisting of (1,2,3)-triazole, (1,2,3)-thiadiazole, (1,2,5)-thiadiazole, and (1,2,5)-oxadiazole; and ii) if two of "F", "G" or "J" are heteroatoms, one of said heteroatoms may be oxygen or sulfur;

wherein said fused heteroaromatic rings may optionally be independently substituted on any of the carbon or nitrogen atoms capable of forming an additional bond with a substituent selected from hydrogen, $(C_1-C_6)$alkyl, halogen, trifluoromethyl, amino-$(CH_2)_n$—, $(C_1-C_6)$alkylamino-$(CH_2)_n$—, di$(C_1-C_6)$alkyl-amino-$(CH_2)_n$—, $(C_1-C_6)$alkoxy, hydroxy$(C_1-C_6)$alkyl, $(C_1-C_6)$alkyl-O-$(C_1-C_6)$alkyl-, —CN, $(C_1-C_6)$alkyl-CO—O—$(C_1-C_6)$alkyl-, $(C_1-C_6)$alkyl-O—CO—O—$(C_1-C_6)$alkyl, $(C_1-C_6)$alkyl-CO—O—, hydroxy, —NO$_2$, $R^3$—C(=O)—, $R^4$—O—C(=O)—, di$(C_1-C_6)$alkyl-N—C(=O)—, $(C_1-C_6)$cycloalkyl, and $R^4$—NH—C(=O)—, and phenyl optionally substituted with halo, $(C_1C_6)$alkyl, —CN, or —CF$_3$;

$R^1$ is optionally substituted phenyl of the formula Ph$^1$ or heteroaryl wherein said heteroaryl is selected from the group consisting of pyridin-2-yl, pyridin-3-yl, pyridin-4-yl, wherein said heteroaryl may optionally be substituted on any of the atoms capable of forming an additional bond, up to a maximum of three substituents, with a substituent selected from hydrogen, $(C_1-C_6)$alkyl, halogen, trifluoromethyl, amino-$(CH_2)_n$—, $(C_1-C_6)$alkylamino-$(CH_2)_n$—, di$(C_1-C_6)$alkyl-amino-$(CH_2)_n$—, $(C_1-C_6)$alkoxy, hydroxy$(C_1-C_6)$alkyl-, $(C_1-C_6)$alkyl-O—$(C_1-C_6)$alkyl-, —CN,$(C_1-C_6)$alkyl-CO—O—$(C_1-C_6)$alkyl-, $(C_1-C_6)$alkyl-O—CO—O—$(C_1-C_6)$alkyl, $(C_1-C_6)$alkyl-CO—O—, hydroxy, H—C(=O)—, $(C_1-C_6)$alkyl-C(=O)—, HO—C(=O)—, $(C_1-C_6)$alkyl-O—C=O)—, NH$_2$—C(=O)—, $(C_1-C_6)$alkyl-NH—C(=O)—, and di$(C_1-C_6)$alkyl-NH—C(=O)—;

wherein said Ph$^1$ is a group of the formula $R^2$ is phenyl of the formula Ph$^2$ or a five or six membered heterocycle, wherein said 6-membered heterocycle has the formula wherein "N" is nitrogen; wherein said ring positions "K", "L" and "M" may be independently selected from carbon or nitrogen, with the proviso that only one of "K", "L" or "M" can be nitrogen;

wherein said five membered heterocycle has the formula wherein said ring positions "P," "Q" and "T" may be independently selected from carbon, nitrogen, oxygen or sulfur; with the proviso that only one of "P," "Q" or "T" can be oxygen or sulfur and at least one of "P," "Q" or "T" must be a heteroatom;

wherein said Ph$^2$ is a group of the formula $R^3$ is hydrogen or $(C_1-C_6)$ alkyl;

$R^4$ is hydrogen or $(C_1-C_6)$ alkyl;

$R^5$ is hydrogen, $(C_1-C_6)$alkyl, halo, CF$_3$, $(C_1-C_6)$alkoxy or $(C_1-C_6)$alkylthiol;

$R^6$ is hydrogen or halo;

$R^7$ is hydrogen or halo;

$R^8$ is hydrogen or halo;

$R^9$ is hydrogen, $(C_1-C_6)$alkyl optionally substituted with one to three halogen atoms, halo, CF$_3$, $(C_1-C_6)$alkoxy optionally substituted with one to three halogen atoms, $(C_1-C_6)$alkylthiol, $R^{13}O$—$(CH_2)_p$—, $(C_1-C_6)$alkyl-NH—$(CH_2)_p$—, di$(C_1-C_6)$alkyl-N—$(CH_2)_p$—, $(C_1-C_5)$cycloalkyl-NH—$(CH_2)_p$13 , H$_2$N—(C=O)—$(CH_2)_p$—, $C_1$-$C_6$alkyl-HN—(C=O)—$(CH_2)_p$—, di$(C_1-C_6)$alkyl-N—(C=O)—$(CH_2)_p$—, $(C_1-C_5)$cycloalkyl-NH—(C=O)—$(CH_2)_p$—, $R^{13}O$—(C=O)—$(CH_2)_p$—, $(C_1-C_6)$alkyl-(O=C)—O—$(C_1-C_6)$alkyl-, $(C_1-C_6)$alkyl-O—(O=C)—O—$(C_1-C_6)$- alkyl-, $(C_1-C_6)$alkyl-(O=C)—O—, $(C_1-C_6)$alkyl-(O=C)—NH—$(CH_2)_p$—, H(O=C)—NH—$(CH_2)_p$—, $(C_1-C_6)$alkyl-(O=C)—N—$(CH_2)_p$—
                              |
                         $(C_1-C_6)$alkyl , -continued

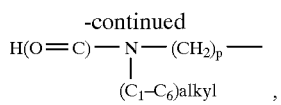

hydroxy, H—C(=O)—(CH$_2$)$_p$—, (C$_1$-C$_6$)alkyl-C(=O)—, (C$_1$-C$_6$)alkyl-O—C(=O)—, R$^4$—(CH$_2$)$_p$—O—C(=O)—, amino-(CH$_2$)$_p$—, hydroxy-(C$_1$-C$_6$)alkyl-, (C$_1$-C$_6$)alkyl-O—(C$_1$-C$_6$)alkyl-, and —CN;

R$^{10}$ and R$^{14}$ are hydrogen, (C$_1$-C$_6$)alkyl optionally substituted with one to three halogen atoms, halo, CF$_3$, (C$_1$-C$_6$) alkoxy optionally substituted with one to three halogen atoms, (C$_1$-C$_6$)alkylthiol, R$^{13}$O—(CH$_2$)$_p$—,(C$_1$-C$_6$)alkyl-NH—(CH$_2$)$_p$—, di(C$_1$-C$_6$)alkyl-N—(CH$_2$)$_p$—, (C$_1$-C$_5$)cycloalkyl-NH—(CH$_2$)$_p$—, H$_2$N—(=O)—(CH$_2$)$_p$—, (C$_1$-C$_6$)alkyl-HN—(C=O)—(CH$_2$)$_p$—, di(C$_1$-C$_6$)alkyl-N—(=O)—(CH$_2$)$_p$—, (C$_1$-C$_5$)cycloalkyl-NH—)C=O)—(CH$_2$)$_p$—, R$^{13}$O—(C=O)—(CH$_2$)$_p$—, (C$_1$-C$_6$)alkyl-(O=C)—O—(C$_1$-C$_6$)alkyl-, (C$_1$-C$_6$)alkyl-O—(O=C)—O—(C$_1$-C$_6$)-alkyl-, (C$_1$-C$_6$)alkyl-(O=C)—O—, (C$_1$-C$_6$) alkyl-(O=C)—NH—(CH$_2$)$_p$—, H(O=C)—NH—(CH$_2$)$_p$—,

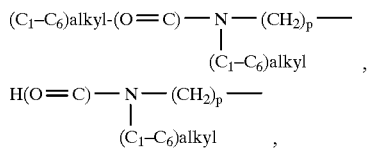

hydroxy, H—C(=O)—(CH$_2$)$_p$—, (C$_1$-C$_6$)alkyl-C(=O)—, (C$_1$-C$_6$)alkyl-O—C(=O)—, R$^4$-(CH$_2$)$_p$—O—(C(=O)—, amino-(CH$_2$)$_p$—, hydroxy-(C$_1$-C$_6$)alkyl-, (C$_1$-C$_6$)-O—(C$_1$-C$_6$)alkyl-, —CHO and —CN;

R$^{11}$ is hydrogen or halo;

R$^{12}$ is hydrogen or halo;

R$^{13}$ is hydrogen, (C$_1$-C$_6$)alkyl, (C$_1$-C$_6$)alkyl-(C=O)—, (C$_1$-C$_6$)alkyl-O—(C=O)—, (C$_1$-C$_6$)alkyl-NH—(C=O)—, or di(C$_1$-C$_6$)alkyl-N—(C=O)—;

R$^{15}$ is hydrogen, —CN, (C$_1$-C$_6$)alkyl, halo, CF$_3$, —CHO or (C$_1$-C$_6$)alkoxy;

R$^{16}$ is hydrogen, —CN, (C$_1$-C$_6$)alkyl, halo, CF$_3$, —CHO or (C$_1$-C$_6$)alkoxy;

R$^{17}$ is hydrogen, —CN, (C$_1$-C$_6$)alkyl, halo, CF$_3$, —CHO or (C$_1$-C$_6$)alkoxy;

n is an integer from zero to 3;

p is an integer from zero to 3;

wherein the dashed bond represented an optional double bond;

with the proviso that when R$^9$ is hydrogen one of R$^{11}$ and R$^{12}$ is other than hydrogen;

and the pharmaceutically acceptable salts of such compounds.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines.

The present invention also relates to compounds of the formula I wherein the "A", "D" or "E" atom of the 6-membered heteroaromatic ring are nitrogen or the "G" or "F" heteroatoms of the 5-membered heteroaromatic ring are sulfur.

Preferred compounds of the formula I are those wherein the A ring is a 5-membered heteroaromatic ring and "G" is sulfur and "F" and "J" are carbon.

Other preferred compounds of the formula I are those wherein the A ring is a 5-membered heteroaromatic ring and "F" is sulfur and "G" and "J" are carbon.

Other preferred compounds of formula I wherein R$^1$ is Ph$^1$ are those wherein one of R$^5$, R$^6$, R$^7$ or R$^8$ is fluoro, bromo, chloro, methyl or trifluoromethyl, preferably R$^5$ is fluoro, bromo, chloro, methyl or trifluoromethyl.

Other preferred compounds of formula I wherein R$^2$ is Ph$^2$ are those wherein R$^9$ is fluoro, chloro, —CN or hydroxy; or R$^{10}$ is —CHO, chloro, fluoro, methyl, (C$_1$-C$_6$)alkyl-NH—(CH$_2$)$_p$—, di(C$_1$-C$_6$)alkyl-N—(CH$_2$)$_p$—, or cyano.

Other preferred compounds of formula I wherein R$^1$ is heteroaryl are those wherein heteroaryl is pyridin-3-yl, optionally substituted with halo, —CN, CF$_3$, or (C$_1$-C$_6$) alkyl, preferably chloro or methyl, more preferably substituted at the 2-position.

Other preferred compounds of formula I wherein R$^2$ is heteroaryl are those wherein heteroaryl is optionally substituted pyrid-2-yl, 1,3-thiazol4-yl, 1,3-thiazol-2-yl or fur-2-yl, preferably pyrid-2-yl optionally substituted with —CHO, chloro, fluoro, methyl, (C$_1$-C$_6$)alkyl-NH—(CH$_2$)$_p$—, di(C$_1$-C$_6$)alkyl-N—(CH$_2$)$_p$—, or cyano; 1,3-thiazol-4-yl substituted with chloro, fluoro, methyl or cyano; or 1,3-thiazol-2-yl substituted in the 4-position with methyl.

Most preferred compounds of formula I, wherein G is sulfur and F and J are carbon, are those wherein:

R$^1$ is Ph$^1$ and R$^5$ is methyl, chloro, trifluoromethyl or bromo; and

R$^2$ is phenyl, pyridin-2-yl, (1,3)-thiazol-2-yl or (1,3)-thiazol4-yl; wherein said phenyl is Ph$^2$ and R$^9$ is chloro, fluoro, —CN or hydroxy; said pyridin-2-yl is optionally substituted with methyl, —CN, (C$_1$-C$_6$)alkyl-NH—(CH$_2$)$_p$—, di(C$_{-C6}$)alkyl-N—(CH$_2$)$_p$—, more preferably substituted at the 6-position with methyl or at the 3-position with —CN; said (1,3)-thiazol-2-yl is optionally substituted at the 2-position with —CH$_3$; and said (1,3)-thiazol4-yl is optionally substituted at the 2-position with —CH$_3$;

Most preferred compounds of formula I wherein F is sulfur and G and J are carbon are those wherein:

R$^1$ is Ph$^1$ and R$^5$ is methyl or chloro; and

R$^2$ is Ph$^2$ and R$^9$ is fluoro or —CN, or pyridin-2-yl optionally substituted with methyl, —CN, (C$_1$-C$_6$)alkyl-NH—(CH$_2$)$_p$— or di(C$_1$-C$_6$)alkyl-N—(CH$_2$)$_p$—.

Specific preferred compounds of formula I are:

3-(2-chlorophenyl)-2-[2-(2-fluoro-phenyl)-vinyl]-3H-thieno[3,2-d]pyrimidin-4one;

3-(2-methylphenyl)-2-[2-chlorophenyl-vinyl]-3H-thieno[3, 2-d]pyrimidin-4-one;

3-(2-trifluoromethyl-phenyl)-2-[2-fluorophenyl-vinyl]-3H-thieno[3,2-d]pyrimidin-4-one;
3-(2-chloropyrid-3-yl)-2-[2-fluorophenyl-vinyl]-3H-thieno[3,2-d]pyrimidin-4-one;
3-(2-methylphenyl)-2-[6-carboxaldehyde-pyrid-2-yl-vinyl]-3H-thieno[3,2-d]pyrimidin-4-one;
3-(2-methylpyrid-3-yl)-2-[2-fluorophenyl-vinyl]-3H-thieno[3,2-d]pyrimidin-4-one;
3-(2-chlorophenyl)-2-(2-pyridin-2-yl-vinyl)-3H-thieno[3,4-d]pyrimidin-4-one;
3-(2-methylphenyl)-2-(2-fluorophenyl-vinyl)-3H-thieno[3,4-d]pyrimidin-4-one;
3-(2-methylphenyl)-2-[2-(2-fluoro-phenyl)-vinyl]-3H-thieno[3,2-d]pyrimidin-4-one;
3-(2-chloro-pyridin-3-yl)-2-[2-(2-methyl-thiazol-4-yl)-vinyl]-3H-thieno[3,2-d]pyrimidin-4-one;
3-(2-methyl-pyridin-3-yl)-2-[2-(2-methyl-thiazol-4-yl)-vinyl]-3H-thieno[3,2-d]pyrimidin-4-one;
3-(2-chlorophenyl)-2-[2-hydroxyphenyl-vinyl]-3H-thieno[3,2-d]pyrimidin-4-one; and
3-(2-chlorophenyl)-2-[2-pyrid-2-yl-vinyl]-3H-thieno[3,2-d]pyrimidin-4-one.

Specific compounds of the invention are:

3-(2-methylphenyl)-2-[2-bromophenyl-vinyl]-3H-thieno[3,2-d]pyrimidin-4-one;
3-(2-chlorophenyl)-2-[2-methoxyphenyl-vinyl]-3H-thieno[3,2-d]pyrimidin-4-one;
3-(2-chlorophenyl)-2-[4-methoxyphenyl-vinyl]-3H-thieno[3,2-d]pyrimidin-4-one;
3-(2-methylphenyl)-2-[4-carbomethoxyphen yl-vinyl]-3H-thieno[3,2-d]pyrimidin-4-one;
3-(2-methylphenyl)-2-[2-pyrid-2-yl-vinyl]-3H-thieno[3,2-d]pyrimidin-4-one;
3-(2-bromophenyl)-2-[2-pyrid-2-yl-vinyl]-3H-thieno[3,2-d]pyrimidin-4-one;
3-(2-methylphenyl)-2-[2-methoxyphenyl-vinyl]-3H-thieno[3,2-d]pyrimidin-4-one;
3-(2-methylphenyl)-2-[2-hydroxyphenyl-vinyl]-3H-thieno[3,2-d]pyrimidin-4-one;
3-(2-methylphenyl)-2-(2-pyridin-2-yl-vinyl)-3H-thieno[3,4-d]pyrimidin-4-one;
2-[2-(2-fluoro-phenyl)-vinyl]-3-o-tolyl-3H-pteridin-4-one;
3-(2-methylphenyl)-2-(2-pyridin-2-yl-vinyl)-3H-pteridin-4-one;
3-(2-chlorophenyl)-2-(2-fluorophenyl-vinyl)-3H-pteridin-4-one;
3-(2-chlorophenyl)-2-(2-pyridin-2-yl-vinyl)-3H-pteridin-4-one;
2-[2-(2-fluoro-phenyl)-vinyl]-3-o-tolyl-3H-pyrido[3,4-d]pyrimidin-4-one;
3-(2-chloro-phenyl)-2-(2-pyridin-2-yl-ethyl)-3H-thieno[3,2-d]pyrimidin-4-one;
3-(2-methyl-phenyl)-2-(2-fluorophenyl-ethyl)-3H-thieno[3,2-d]pyrimidin-4-one;
3-(2-methyl-phenyl)-2-(2-pyridin-2-yl-ethyl)-3H-thieno[3,2-d]pyrimidin-4-one;
3-(2-methyl-phenyl)-2-(2-pyridin-2-yl-ethyl)-3H-thieno[3,4-d]pyrimidin-4-one;
3-(2-chloro-phenyl)-2-(2-pyridin-2-yl-ethyl)-3H-thieno[3,4-d]pyrimidin-4-one;
5-(2-pyridin-2-yl-vinyl)-6-o-tolyl-3,6-dihydro-[1,2,3]triazolo[4,5-d]pyrimidin-7-one;
2-[2-(2-fluorophenyl)-vinyl]-6-methyl-3-o-tolyl-3H-thieno[3,2-d]pyrimidin-4-one;
3-(2-chlorophenyl)-2-[2-(2-fluoro phenyl)-vinyl]-5-methyl-3H-thieno[3,4-d]pyrimidin-4-one;
2-[2-(2-fluorophenyl)-vinyl]-6-methyl-3-(2-chlorophenyl)-3H-thieno[3,2-d]pyrimidin-4-one;
3-(2-methylphenyl)-2-[2-(2-fluorophenyl)-vinyl]-5-methyl-3H-thieno[3,4-d]pyrimidin-4-one;
2-[2-(2-hydroxyphenyl)-vinyl]-6-methyl-3-o-tolyl-3H-thieno[3,2-d]pyrimidin-
3-(2-chlorophenyl)-2-[2-(2-hydroxyphenyl)-vinyl]-5-methyl-3H-thieno[3,4-d]pyrimidin-4-one;
2-[2-(2-hydroxyphenyl)-vinyl]-6-methyl-3-(2-chlorophenyl)-3H-thieno[3,2-d]pyrimidin-4-one;
3-(2-methylphenyl)-2-[2-(2-hydroxyphenyl)-vinyl]-5-methyl-3H-thieno[3,4-d]pyrimidin-4-one;
2-[2-(2-chlorophenyl)-vinyl]-6-methyl-3-o-tolyl-3H-thieno[3,2-d]pyrimidin-4-one;
3-(2-chlorophenyl)-2-[2-(2-chlorophenyl)-vinyl]-5-methyl-3H-thieno[3,4-d]pyrimidin-4-one;
2-[2-(2-chloropheny)-vinyl]-6-methyl-3-(2-chlorophenyl)-3H-thieno [3,2-d]pyrimidin-4-one;
3-(2-methylphenyl)-2-[2-(2-chlorophenyl)-vinyl]-5-methyl-3H-thieno[3,4-d]pyrimidin-4-one;
2-[2-(2-fluorophenyl)-vinyl]-6-methyl-3-(2-trifluoromethylphenyl)-3H-thieno[3,2-d]pyrimidin-4-one;
3-(2-trifluorophenyl)-2-[2-(2-fluorophenyl)-vinyl]-5-methyl-3H-thieno[3,4-d]pyrimidin-4-one;
2-[2-(2-fluorophenyl)-vinyl]-6-methyl-3-(2-chloropyridin-3-yl)-3H-thieno[3,2-d]pyrimidin-4-one;
3-(2-methylpyridin-3-yl)-2-[2-(2-fluorophenyl)-vinyl]-5-methyl-3H-thieno[3,4-d]pyrimidin-4-one;
2-[2-(2-hydroxyphenyl)-vinyl]-6-methyl-3-(2-trifluoromethylphenyl)-3H-thieno[3,2-d]pyrimidin-4-one;
3-(2-trifluorophenyl)-2-[2-(2-hydroxyphenyl)-vinyl]-5-methyl-3H-thieno[3,4-d]pyrimidin-4-one;
2-[2-(2-hydroxyphenyl)-vinyl]-6-methyl-3-(2-chloropyridin-3-yl)-3H-thieno[3,2-d]pyrimidin-4-one;
3-(2-methylpyridin-3-yl)-2-[2-(2-hydroxyphenyl)-vinyl]-5-methyl-3H-thieno[3,4-d]pyrimidin-4-one;
2-[2-(2-chlorophenyl)-vinyl]-6-methyl-3-(2-chloro-pyridin-3-yl)-3H-thieno[3,2-d]pyrimidin-4-one;
3-(2-chloropyridin-3-yl)-2-[2-(2-chlorophenyl)-vinyl]-5-methyl-3H-thieno[3,4-d]pyrimidin-4-one;
2-[2-(2-chlorophenyl)-vinyl]-6-methyl-3-(pyridin-3)-3H-thieno[3,2-d]pyrimidin-4-one;
3-(2-methylphenyl)-2-[2-(pyridin-2yl)-vinyl]-5-methyl-3H-thieno[3,4-d]pyrimidine-4-one;
3-(2-chlorophenyl)-2-[1,3-thiazol-4-yl-vinyl]-6-methyl-3H-thieno[3,2-d]pyrimidin-4-one;
3-(2-methylphenyl)-2-[1,3-thiazol-4-yl-vinyl]-5-methyl-3H-thieno[3,4-d]pyrimidin-4-one;
3-(2-chlorophenyl)-2-[1,3-thiazol-2- yl-vinyl]-6-chloro-3H-thieno[3,2-d]pyrimidin-4-one;
3-(2-methylphenyl)-2-[1,3-thiazol-2-yl-vinyl]-5-chloro-3H-thieno[3,2-d]pyrimidin-4-one;
3-(2-chlorophenyl)-2-[1,3-thiazol-4-yl-vinyl]-3H-thieno[3,2-d]pyrimidin-4-one;
3-(2-methylphenyl)-2-[1,3-thiazol-4-yl-vinyl]-3H-thieno[3,2-d]pyrimidin-4-one;
3-(2-chlorophenyl)-2-[1,3-thiazol-2-yl-vinyl]-3H-thieno[3,2-d]pyrimidin-4-one;
3-(2-methylphenyl)-2-[1,3-thiazol-2-yl-vinyl]-3H-thieno[3,2-d]pyrimidin-4-one;
3-(2-chlorophenyl)-2-[2-(2-cyanophenyl)-vinyl]-3H-thieno[3,2-d]pyrimidin-4-one;
3-(2-methylphenyl)-2-[2-cyanophenyl-vinyl]-3H-thieno[3,2-d]pyrimidin-4-one;
3-(2-trifluoromethyl-phenyl)-2-[2-cyanop henyl-vinyl]-3H-thieno[3,2-d]pyrimidin-4-one;

3-(2-cyloropyrid-3-yl)-2-[2-cyanophenyl-vinyl]-3H-thieno[3,2-d]pyrimidin-4-one;

3-(2-methylphenyl)-2-[6-cyano-pyrid-2-yl-vinyl]-3H-thieno[3,2-d]pyrimidin-4-one;

3-(2-methylpyrid-3-yl)-2-[2-cyanophenyl-vinyl]-3H-thieno[3,2-d]pyrimidin-4-one;

3-(2-chlorophenyl)-2-(2-cyanopyridin-2-yl-vinyl)-3H-thieno[3,4-d]pyrimidin-4-one;

3-(2-methylphenyl)-2-(2-cyanophenyl-vinyl)-3H-thieno[3,4-d]pyrimidin-4-one;

3-(2-methylphenyl)-2-[2-(2-cyano-phenyl)-vinyl]-3H-thieno[3,2-d]pyrimidin-4-one;

3-(2-chlorophenyl)-2-[2-cyanopyrid-2-yl-vinyl]-3H-thieno[3,2-d]pyrimidin-4-one; and 3-(2-chlorophenyl)-2-[2-hydroxyphenyl-vinyl-]-3H-thieno[3,2-d]pyrimidin-4-one.

This invention also relates to a pharmaceutical composition for treating or preventing a condition selected from cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced demential, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, or tardive dyskinesia, in a mammal, comprising an amount of a compound of formula I effective in treating or preventing such condition and a pharmaceutically acceptable carrier.

This invention also relates to a method of treating or preventing a condition selected from cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced demential, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, or tardive dyskinesia, in a mammal, comprising administering to a mammal in need of such treatment or prevention an amount of a compound of formula I effective in treating or preventing such condition.

This invention also relates to a pharmaceutical composition for treating or preventing disorders the treatment or prevention of which is facilitated by enhanced glutamate neurotransmission in a mammal, comprising an amount of a compound of formula I effective in treating or preventing such condition and a pharmaceutically acceptable carrier.

This invention also relates to a method of treating or preventing disorders the treatment or prevention of which is facilitated by enhanced glutamate neurotransmission in a mammal, comprising administering to a mammal in need of such treatment or prevention an amount of a compound of formula I effective in treating or preventing such condition.

This invention also relates to a pharmaceutical composition for treating or preventing a condition selected from cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced demential, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, or tardive dyskinesia, in a mammal, comprising an AMPA receptor antagonizing effective amount of a compound of formula I and a pharmaceutically acceptable carrier.

This invention also relates to a method for treating or preventing a condition selected from cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced demential, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, or tardive dyskinesia, in a mammal, comprising administering to a mammal requiring such treatment or prevention an AMPA receptor antagonizing effective amount of a compound of formula I.

This invention also relates to a pharmaceutical composition for treating or preventing disorders the treatment or prevention of which is facilitated by enhanced glutamate neurotransmission in a mammal, comprising an AMPA receptor antagonizing effective amount of a compound of formula I and a pharmaceutically acceptable carrier.

This invention also relates to a method for treating or preventing disorders the treatment or prevention of which is facilitated by enhanced glutamate neurotransmission in a mammal, comprising administering to a mammal requiring such treatment or prevention an AMPA receptor antagonizing effective amount of a compound of formula I.

Unless otherwise indicated, the alkyl groups referred to herein, as well as the alkyl moieties of other groups referred to herein (e.g., alkoxy), may be linear or branched, and they may also be cyclic (e.g., cyclopropyl, cyclobutyl, cyclopentyl, or cyclohexyl) or be linear or branched and contain cyclic moieties.

Compounds of the formula I wherein the fused A ring is a 6-membered aryl heterocycle include compounds wherein the ring positions A, B, D and E assume the following respective atom combinations:

| A | B | D | E |
|---|---|---|---|
| Nitrogen | Carbon | Carbon | Carbon |
| Carbon | Nitrogen | Carbon | Carbon |
| Carbon | Carbon | Nitrogen | Carbon |
| Nitrogen | Carbon | Nitrogen | Carbon |
| Carbon | Nitrogen | Carbon | Nitrogen |
| Nitrogen | Nitrogen | Carbon | Carbon |
| Carbon | Nitrogen | Nitrogen | Carbon |
| Carbon | Carbon | Nitrogen | Nitrogen |

Compounds of the formula I wherein the fused A ring is a 5-membered aryl heterocycle includes compounds wherein the heteroatom combinations assume the following respective atom combinations:

| F | G | J |
|---|---|---|
| Nitrogen, | Carbon, | Carbon; |
| Carbon, | Nitrogen, | Carbon; |
| Carbon, | Carbon, | Nitrogen; |
| Nitrogen, | Nitrogen, | Carbon; |
| Nitrogen, | Carbon, | Nitrogen; |
| Carbon, | Nitrogen, | Nitrogen; |
| Nitrogen, | Nitrogen, | Nitrogen; |
| Oxygen, | Carbon, | Carbon; |
| Carbon, | Oxygen, | Carbon; |
| Carbon, | Carbon, | Oxygen; |
| Sulfur, | Carbon, | Carbon, |
| Carbon, | Sulfur | Carbon; |
| Carbon, | Carbon, | Sulfur; |
| Nitrogen, | Oxygen, | Carbon; |
| Nitrogen, | Carbon, | Oxygen; |
| Oxygen, | Nitrogen, | Carbon; |
| Oxygen, | Carbon, | Nitrogen; |
| Carbon, | Oxygen, | Nitrogen; |
| Carbon, | Nitrogen | Oxygen |
| Nitrogen, | Sulfur, | Carbon |
| Nitrogen, | Carbon, | Sulfur; |
| Sulfur, | Nitrogen, | Carbon; |
| Sulfur, | Carbon, | Nitrogen; |
| Carbon, | Sulfur, | Nitrogen; |
| Carbon, | Nitrogen, | Sulfur; |
| Nitrogen | Nitrogen | Sulfur; |
| Nitrogen | Sulfur | Nitrogen |
| Nitrogen | Oxygen | Nitrogen |

When $R^2$ is heteroaryl, one of ordinary skill in the art will understand that heteroaryl includes substituted or unsubstituted pyridin-2-yl, 1,3-pyrazin-4-yl, 1,4-pyrazin-2-yl, 1,3-pyrimidin-2-yl, pyrrol-2-yl, 1,3-imidazol-4-yl, 1,3-imidazol-2-yl, 1,3,4-triazol-2-yl, 1,3-oxazol-4-yl, 1,3-oxazol-2-yl, 1,3-thiazol-4-yl, 1,3-thiazol-2-yl, 1,2,4-oxadiazol-3-yl, 1,2,4-oxadiazol-5-yl, fur-2-yl, 1,3-oxazol-5-yl, and 1,3,4-oxadiazol-2-yl, wherein said heteroaryl may optionally be substituted on any of the atoms capable of forming an additional bond, up to a maximum of three substituents.

DETAILED DESCRIPTION OF THE INVENTION

The compounds of formula I can be prepared according to the methods of Schemes 1 and 2. In the reaction Scheme and discussion that follow, A, B, D, E, F, G, J, K, L, M, P, Q, T, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $Ph^1$, $Ph^2$, n, m, and p, unless otherwise indicated, are as defined above for formula I.

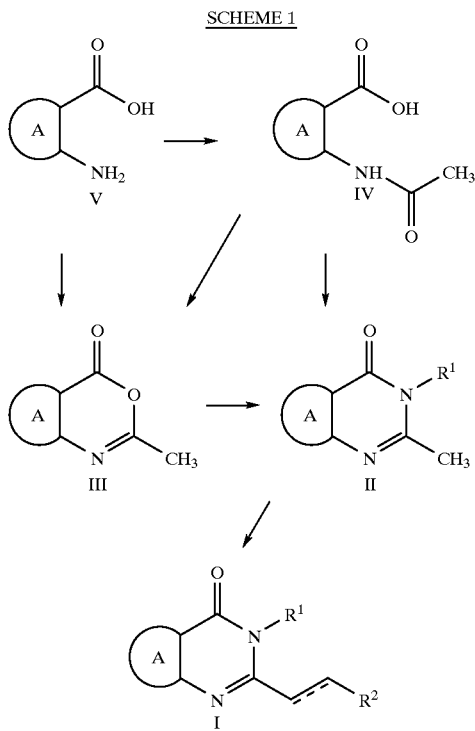

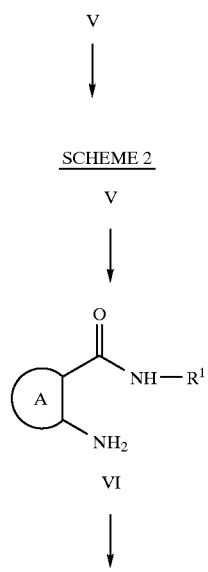

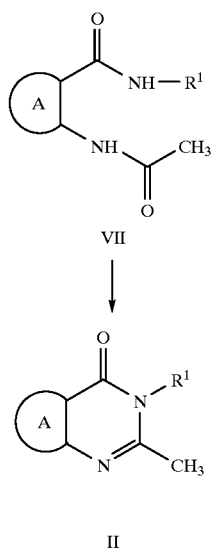

Scheme 1 refers to the preparation of compounds of the formula I from compounds of the formula V. Compounds of the formula V are commercially available or can be prepared by methods well known to those of ordinary skill in the art. Compounds of the formula V, wherein "A" is a 4-amino-(1,2)-pyridazine-5-carboxylic acid can be prepared according to the methods described in J. Het. Chem., 14, 1099 (1977); Aust. J. Chem., 22, 1745 (1969); and J. Het. Chem., 5, 845 (1968). Compounds of the formula V wherein "A" is a 4-amino-(1,2)-pyridazine-3-carboxylic acid can be made according to the methods described in J. Het. Chem., 5, 523 (1968). Compounds of the formula V, wherein "A" is 2-amino-(1,2)-pyridazine-3-carboxylic acid can be made according to the methods described in J. Het. Chem., 5, 523 (1968); and J. Org. Chem., 50, 346 (1995). Compounds of the formula V, wherein "A" is 5-amino-(1,2,3)-thiazdiazole-4-carboxylic acid can be prepared according to the methods described in Chem. Berichte, 99,1618 (1966). Compounds of the formula V, wherein "A" is 4-amino-(1,2,5)-thiadiazole-3-carboxylic acid can be made according to the methods described in J. Med. Chem., 22, 944 (1979) and Tetrahedron Lett., 2143 (1971). Compounds of the formula V, wherein "A" is 4-amino-(1,2,5)-oxadiazole-3-carboxylic acid can be made according to the methods described in Heterocycles, 20, 2351 (1983). Compounds of the formula V, wherein "A" is 3-amino-thiophene-2-carboxylic acid can be prepared according to the method described in European Patent publication 269,295 published Jun. 1, 1988.

A compound of the formula V can be converted into an acetamide of the formula IV by reaction with acetyl chloride or acetic anhydride in the presence of a base in a reaction inert solvent. Suitable solvents include methylene chloride, dichloroethane, tetrahydrofuran and dioxane, preferably methylene chloride. Suitable bases include trialkylamines such as triethylamine and tributylamine, dimethylaminopyridine and potassium carbonate, preferably triethylamine. The temperature of the aforesaid reaction is in the range from about 0° C. to about 35° C. for about 1 hour to about 10 hours, preferably at about 30° C. for about 3 hours.

The acetamide of the formula IV is cyclized to a compound of the formula III by reaction with a dehydrating agent, in the presence of a catalyst, in dry reaction inert solvent. Suitable dehydrating agents include acetic anhydride, phosphrous pentoxide, dicyclohexylcarbodiimide, and acetyl chloride, preferably acetic anhydride. Suitable catalysts include sodium or potassium acetate, acetic acid, p-toluene sulfonic acid, or boron trifluoride etherate, preferably sodium acetate. Suitable solvents include dioxane, toluene, diglyme or dichloroethane, preferably dioxane. The temperature of the aforesaid reaction is in the range from about 80° C. to about 110° C. for about 1 hour to about 24 hours, preferably at about 100° C. for about 3 to 10 hours.

Alternatively, the compound of formula V can be directly converted into a compound of formula III by reaction with acetic anhydride in the presence of an acid catalyst in a solvent. Suitable acid catalysts include acetic acid, sulfuric acid, or p-toluene sulfonic acid, preferably acetic acid. Suitable solvents include acetic acid, toluene or xylene, preferably acetic acid. The temperature of the aforesaid reaction is from about 20° C. to about 150° C. for about 10 minutes to about 10 hours, preferably at about 120° C. for about 2 to 5 hours.

The compound of formula III, formed by either of the above methods, is reacted with an amine of the formula $R^1NH_2$ in a polar protic solvent in the presence of an acid catalyst to form a compound of the formula II. Suitable acid catalysts include acetic acid, p-toluene sulfonic acid or sulfuric acid, preferably acetic acid. Suitable polar protic solvents include acetic acid, methanol, ethanol or isopropanol, preferably acetic acid. The temperature of the aforesaid reaction is from about 20° C. to about 117° C. for about 1 hour to about 24 hours, preferably at about 117° C. for about 6 hours.

Alternatively, a compound of the formula IV can be directly converted to a compound of the formula II by reaction with a dehydrating agent, an amine of the formula $R^1NH_2$, and a base, in a reaction inert solvent. Suitable dehydrating agents include phosphorous trichloride, phosphorous oxychloride, phosphorous pentachloride or thionyl chloride, preferably phosphorous trichloride. Suitable bases include pyridine, lutidine, dimethylaminopyridine, triethylamine or N-methyl morpholine, preferably pyridine. Suitable solvents include toluene, cyclohexane, benzene or xylene, preferably toluene. Under some circumstances, when the combined reactants are a liquid, the reaction may be run neat. The temperature of the aforesaid reaction is from about 50° C. to about 150° C. for about 1 hour to about 24 hours, preferably at about 110° C. for about 4 hours.

The compound of formula II is reacted with an aldehyde of the formula $R^2CHO$ in the presence of a catalyst and a dehydrating agent in a suitable solvent to form a compound of the formula I. Suitable catalysts include zinc chloride, aluminum chloride, tin chloride, or boron trifluoride etherate, preferably zinc chloride. Suitable dehydrating agents include acetic anhydride or propionic anhydride, preferably acetic anhydride. Suitable polar solvents include acetic acid or propionic acid. The temperature of the aforesaid reaction is from about 60° C. to about 100° C. for about 30 minutes to about 24 hours, preferably at about 100° C. for about 3 hours.

Alternatively, a compound of the formula V can be converted to a compound of the formula 11 according to the methods described in Scheme 2. The compound of formula II, so formed, can be converted into a compound of formula I according to the methods of Scheme 1. Referring to Scheme 2, a compound of the formula V is reacted with a coupling reagent, an amine of the formula $R^1NH_2$, and a base in a reaction inert solvent to form a compound of the formula VI. Examples of suitable coupling reagents which activate the carboxylic functionality are dicyclohexylcarbodiimide, N-3-dimethylaminopropyl-N'-ethylcarbodiimide, 2-ethoxy-1-ethoxycarbonyl-1,2-dihydroquinoline (EEDQ), carbonyl diimidazole (CDI), and diethylphosphorylcyanide. Suitable bases include dimethylaminopyridine (DMAP), hydroxybenzotriazole (HBT), or triethylamine, preferably dimethylaminopyridine. The coupling is conducted in an inert solvent, preferably an aprotic solvent. Suitable solvents include acetonitrile, dichloromethane, dichloroethane, and dimethylformamide. The preferred solvent is dichloromethane. The temperature of the aforesaid reaction is generally from about −30 to about 80° C., preferably about 0 to about 25° C.

The compound of formula VI is converted into a compound of the formula VII by reaction with acetyl chloride or acetic anhydride in the presence of a base in a reaction inert solvent. Suitable solvents include methylene chloride, tetrahydrofuran and chloroform, preferably methylene chloride. Suitable bases include trialkylamines such as triethylamine and tributylamine, dimethylaminopyridine and potassium carbonate, preferably triethylamine. The temperature of the aforesaid reaction is in the range from about 0° C. to about 35° C. for about 1 hour to about 10 hours, preferably at about 30° C. for about 3 hours.

The compound of formula VII is cyclized to a compound of formula II by reaction with triphenylphosphine, a base, and a dialkyl azodicarboxylate in a reaction inert solvent. Suitable bases include pyridine, triethylamine and 4-dimethylaminopyridine, preferably 4-dimethylaminopyridine. Suitable solvents include dimethylformamide, tetrahydrofuran and dioxane, preferably dioxane. The temperature of the aforesaid reaction is in the range from about 25° C. to about 125° C. for about 1 hour to about 24 hours, preferably at about 100° C. for about 8 to 15 hours. The compound of formula II can be converted into a compound of formula I according to the method described in Scheme 1.

Compounds of formula II can also be made according to the methods described in Miyashita, et al., *Heterocycles*, 42, 2, 691–699 (1996).

Unless indicated otherwise, the pressure of each of the above reactions is not critical. Generally, the reactions will be conducted at a pressure of about one to about three atmospheres, preferably at ambient pressure (about one atmosphere)

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are acidic in nature are capable of forming base salts with various pharmacologically acceptable cations. Examples of such salts include the alkali metal or alkaline-earth metal salts and particular, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction of maximum product of yields of the desired final product.

The compounds of the formula I and the pharmaceutically acceptable salts thereof (hereinafter, also referred to as the active compounds of the invention) are useful for the treatment of neurodegenerative and CNS-trauma related conditions and are potent AMPA receptor agonists and antagonists. The active compounds of the invention may therefore be used in the treatment or prevention of cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced demential, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, or tardive dyskinesia.

The in vitro and in vivo activity of the compounds of the invention for AMPA receptor antagonism can be determined by methods available to one of ordinary skill in the art. One method for determining the activity of the compounds of the invention is by inhibition of pentylenetetrazol (PTZ)-induced seizures. Another method for determining the activity of the compounds of the invention is by AMPA receptor activation-induced $^{45}Ca^{2+}$ uptake.

One specific method for determining inhibition of pentylenetetrazol (PTZ)-induced seizures is as follows. The activity of the compounds of the invention for inhibition of pentylenetetrazol (PTZ)-induced seizures in mice can be determined according to the following procedure. This assay examines the ability of compounds to block seizures and death produced by PTZ. measures taken are latency to clonic and tonic seizures, and death. $ID_{50}s$ are determined based on percent protection.

Male CD-1 mice from Charles River, weighing 14–16 g on arrival and 25–35 g at the time of testing, serve as subjects for these experiments. Mice are housed 13 per cage under standard laboratory conditions on a L:D/7 a.m.: 7 p.m. lighting cycle for at least 7 days prior to experimentation. Food and water are available ad libitum until the time of testing.

All compounds are administered in a volume of 10 ml/kg. Drug vehicles will depend on compound solubility, but screening will typically be done using saline, distilled water, or E:D:S/5:5:90 (5% emulphor, 5% DMSO, and 90% saline) as the injection vehicle.

Mice are administered the test compounds or vehicle (i.p., s.c., or p.o.) and are placed into plexiglass cages in groups of five. At a predetermined time after these injections, mice are given an injection of PTZ (i.p., 120 mg/kg) and placed into individual plexiglass cages. Measures taken during this five minute test period are: (1) latency to clonic seizures, (2) latency to tonic seizures, and (3) latency to death. Treatment groups are compared to the vehicle-treated group by Kruskal-Wallis Anova and Mann-Whitney U tests (Statview). Percent protection is calculated for each group (number of subjects not showing seizure or death as indicated by a score of 300 secs) at each measure. $ID_{50}$'s are determined by probit analysis (Biostat).

Another method for determining the activity of the compounds is to determine the effect of the compounds on motor coordination in mice. This activity can be determined according to the following procedure.

Male CD-1 mice from Charles River, weighing 14–16 g on arrival and 23–35 g at the time of testing, serve as subjects for these experiments. Mice are housed 13 per cage under standard laboratory conditions on a L:D/7 a.m.: 7 p.m. lighting cycle for at least 7 days prior to experimentation. Food and water are available ad libitum until the time of testing.

All compounds are administered in a volume of 10 ml/kg. Drug vehicles will depend on compound solubility, but screening will typically be done using saline, distilled water, or E:D:S/5:5:90 (5% emulphor, 5% DMSO, and 90% saline) as the injection vehicle.

The apparatus used in these studies consists of a group of five 13.34×13.34 cm wire mesh squares suspended on 11.43 cm steel poles connected to a 165.1 cm pole which is elevated 38.1 cm above the lab bench. These wire mesh squares can be turned upside-down.

Mice are administered test compounds or vehicle (i.p., s.c., or p.o) and are placed into plexiglass cages in groups of five. At a predetermined time after these injections, mice are placed on top of the wire mesh squares and flipped so that they are suspended upside-down. During the one minute test, mice are rated 0 if they fall off the screen,m 1 if they hand on upside-down, or 2 if they climb up onto the top. Treatment groups are compared to the vehicle-treated group with Kruskal-Wallis and Mann-Whitney U tests (Statview).

One specific method for determining AMPA receptor activation-induced $^{45}Ca^{2+}$ uptake is described below.

Neuronal Primary Cultures

Primary cultures of rat cerebellar granule neurons are prepared as described by Parks, T. N., Artman, L. D., Alasti, N., and Nemeth, E. F., Modulation Of N-Methyl-D-Aspartate Receptor-Mediated Increases In Cytosolic Calcium In Cultured Rat Cerebellar Granule Cells, Brain Res. 552, 13–22 (1991). According to this method, cerebella are removed from 8 day old CD rats, minced into 1 mm pieces and incubated for 15 minutes at 37° C. in calcium-magnesium free Tyrode's solution containing 0.1% trypsin. The tissue is then triturated using a fine bore Pasteur pipette. The cell suspension is plated onto poly-D-lysine coated 96-well tissue culture plates at $10^5$ cells per well. Medium consists of Minimal Essential Medium (MEM), with Earle's salts, 10% heat inactivated Fetal Bovine Serum, 2 mM L-glutamine, 21 mM glucose, Penicillin-Streptomycin (100 units per ml) and 25 mM KCl. After 24 hours, the medium is replaced with fresh medium containing 10 µM cytosine arabinoside to inhibit cell division. Cultures should be used at 6–8 DIV.

AMPA Receptor Activation-induced $^{45}Ca^{2+}$ Uptake

The effects of drugs on AMPA receptor activation-induced $^{45}Ca^{2+}$ uptake can be examined in rat cerebellar granule cell cultures. Cultures in 96 well plates are preincubated for approximately 3 hours in serum free medium and then for 10 minutes in a $Mg^{2+}$-free balanced salt solution (in mM: 120 NaCl, 5 KCl, 0.33 $NaH_2PO_4$ 1.8 $CaCl_2$, 22.0 glucose and 10.0 HEPES at pH 7.4) containing 0.5 mM DTT, 10 uM glycine and drugs at 2× final concentration. The reaction is started by rapid addition of an equal volume of the balanced salt solution containing 100 µM of the AMPA receptor agonist kainic acid and $^{45}Ca^{2+}$ (final specific activity 250 Ci/mmol). After 10 minutes at 25° C., the reaction is stopped by aspirating the $^{45}Ca^{2+}$-containing solution and washing the cells 5× in an ice cold balanced salt solution containing no added calcium and 0.5 mM EDTA. Cells are then lysed by overnight incubation in 0.1% Triton-X100 and radioactivity in the lysate is then determined. All of the compounds of the invention, that were tested, had $IC_{50}$s of less than 5 µM.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., stroke) is 0.01 to 50 mg/kg of the active ingredient per unit dose which could be administered, for example, 1 to 4 times per day.

Aerosol formulations for treatment of the conditions referred to above (e.g., stroke) in the average adult human are preferably arranged so that each metered dose or "puff" of aerosol contains 20 $\mu$g to 1000 $\mu$g of the compound of the invention. The overall daily dose with an aerosol will be within the range 100 $\mu$g to 10 mg. Administration may be several times daily, for example 2, 3, 4 or 8 times, giving for example, 1, 2 or 3 doses each time.

The following Examples illustrate the preparation of the compounds of the present invention. Commercial reagents were utilized without further purification. Melting points are uncorrected. NMR data are reported in parts per million ($\delta$) and are referenced to the deuterium lock signal from the sample solvent. Unless otherwise stated, all mass spectrum were performed using chemical impact conditions. Ambient or room temperature refers to 20–25° C.

EXAMPLE 1

3-(2-Methyl-phenyl)-2-[2-(2-fluoro- phenyl)-vinyl-3H-thieno[3,2-d]pyrimidin-4-one Anhydrous zinc chloride (7.0 g, 51.4 mmol) was fused with a nitrogen purge in a round bottom flask with an open flame. The reaction vessel was allowed to return to ambient temperature, then dioxane (100 mL) was added. To this mixture was added 2-methyl-3-(2-methylphenyl)-3H-thieno [3,2-d]pyrimidin-4-one (7.0 g, 27.34 mmol, preparation 2), acetic anhydride (7.7 mL, 82.0 mmol), and 2-fluorobenzaldehyde (8.6 mL, 10.2 mmol). The reaction was refluxed 14 hours, cooled to ambient temperature, and partitioned between ethyl acetate and water. The aqueous layer was extracted with ethyl acetate and the combined organic layer was filtered to obtain a small amount of product which had precipitated. The filtrate was washed with water and brine, dried over magnesium sulfate and concentrated to leave a mustard colored solid. This material was added to the product which had previously been collected and the combined material was flash chromatographed on silica gel (60×185 mm) eluting with 25–40% ethyl acetate/ hexane to afford 5.06 g (51%) of 3-(2-methyl-phenyl)-2-[2-(2-fluoro-phenyl)-vinyl]-3H-thieno[3,2-d]pyrimidin-4-one as a light yellow solid.

Mp 220–221° C.; NMR $\delta$8.03 (d, J=15.8 Hz, 1H), 7.82 (d, J=5.2 Hz, 1H), 7.45–7.37 (m, 4H), 7.25–7.10 (m, 3H), 7.07–6.99 (m, 2H), 6.44 (d, J=15.9 Hz, 1H), 2.11 (s, 3 H). Analysis calculated for $C_2H_{15}FN_2OS$: C, 68.76; H, 4.23; N, 7.64. Found: C, 68.89; H, 4.16; N, 7.72.

EXAMPLE 2

3-(2-Chloro-phenyl)-2-2-(2-fluoro-phenyl)-vinyl]-3H-thieno[3,2-d]pyrimidin-4-one To a mixture of fused zinc chloride (0.35 g, 2.56 mmol) and dioxane (15 mL), 2-methyl-3-(2-chlorophenyl)-3H-thieno[3,2-d]pyrimidin-4-one (0.344 g, 1.24 mmol, preparation 3), and acetic anhydride (0.35 mL, 3.73 mmol) was added 2-fluorobenzaldehyde (0.39 mL, 3.73 mmol). The reaction was refluxed 30 hours, cooled to ambient temperature, and diluted with ethyl acetate and water. The two phase mixture was treated with aqueous sodium bicarbonate until the aqueous layer remained basic. Phases were filtered to remove an insoluble residue, then separated. The aqueous layer was extracted with ethyl acetate and the combined organic layer was washed with water and brine, dried over sodium sulfate and concentrated to leave a brown residue. This material was taken up in ethyl acetate and diluted with hexane until a precipitate (0.153 g, 32%) of 3-(2-chloro-phenyl)-2-[2-(2-fluoro-phenyl)-vinyl]-3H-thieno[3,2-d]pyrimidin-4-one formed, as a yellow solid.

Mp 215–216° C.; NMR $\delta$8.05 (d, J=15.5 Hz, 1H), 7.84 (d, J=5.2 Hz, 1H), 7.65–7.61 (m, 1H), 7.51–7.40 (m, 2H), 7.39–7.36 (m, 1H), 7.29–7.22 (m, 2H), 7.08–7.00 (m, 2H), 6.42 (d, J=15.5 Hz, 1H). Analysis calculated for $C_{20}H_{12}FClN_2OS$: C, 62.75; H, 3.14; N, 7.32. Found: C, 62.45; H, 3.14; N, 7.40.

EXAMPLE 3

3-(2-Methyl-phenyl)-2-[2-pyrid-2-yl-vinyl]-3H-thieno[3,2-d]pyrimidin-4-one

To a mixture of fused zinc chloride (2.13 g, 15.6 mmol) and dioxane (75 mL), 2-methyl-3-(2-methylphenyl)-3H-thieno[3,2-d]pyrimidin-4-one (2.0 g, 7.81 mmol, preparation 2), and acetic anhydride (2.2 mL, 23.4 mmol) was added 2-pyridine carboxaldehyde (2.2 mL, 23.4 mmol). The reaction was refluxed 1.5 hours, cooled to ambient temperature, and diluted with aqueous sodium bicarbonate. The mixture was extracted with ethyl acetate and the organic extracts were washed with water and brine, dried over sodium sulfate and concentrated to leave a dark residue. This material was flash chromatographed on silica gel (45×125 mm). Elution with 20% ethyl acetate/hexane removed an unweighed impurity. Continued elution with 40% ethyl acetate/hexane gave a sticky yellow foam. The foam was triturated with 5% ethyl acetate/hexane to yield 1.9 g (70%) of 3-(2-methyl-phenyl)-2-[2-pyrid-2-yl-vinyl]-3H-thieno[3,2-d]pyrimidin-4-one as a yellow solid.

Mp 203° C.; NMR $\delta$8.47 (d, J=3 Hz, 1H), 7.92 (d, J=14.7 Hz, 1H), 7.82 (d, J=4 Hz, 1H), 7.60 (t, J=8.5 Hz, 1H), 7.43–7.37 (m, 4H), 7.26–7.12 (m, 3H), 6.89 (d, J=14.7 Hz, 1H), 2.10 (s, 3H). Analysis calculated for $C_{20}H_{15}N_3OS$: C, 69.36; H 4.62; N, 12.14. Found: C, 69.10; H, 4.50; N, 12.19.

EXAMPLE 4

The compounds in Table 1 were all made by essentially the same procedure as exemplified in Examples 1–3.

TABLE 1

| $R^2$ | $R^1$ | Physical Data |
|---|---|---|
| 2-chloro-phenyl | 2-methyl-phenyl | mp 198° C.<br>NMR δ 8.29 (d, J = 15.4 Hz, 1 H), 7.82 (d, J = 5.2 Hz, 1 H), 7.43–7.36 (m, 5 H), 7.23–7.12 (m, 4 H), 6.31 (d, J = 15.5 Hz, 1 H), 2.11 (s, 3 H)<br>HRMS $M^{+1}$ calculated m/e = 379.0669. Observed m/e = 379.0684. |
| 2-bromo-phenyl | 2-methyl-phenyl | mp 194° C.<br>NMR δ 8.24 (d, J = 15.5 Hz, 1 H), 7.82 (d, J = 5.3 Hz, 1 H), 7.55 (d, J = 6.6 Hz, 1 H), 7.44–7.37 (m, 4 H), 7.24–7.12 (m, 4 H), 6.27 (d, J = 15.6 Hz, 1 H), 2.11 (s, 3H)<br>Analysis calculated for $C_{21}H_{15}BrN_2OS·H_2O$: C, 57.14; H, 3.85; N, 6.35. Found: C, 57.36; H, 3.59; N, 6.23. |
| 2-fluoro-phenyl | 2-trifluoro-methyl-phenyl | mp 206–207° C.<br>NMR δ 8.01 (d, J = 15.4 Hz, 1 H), 7.93–7.69 (m, 4 H), 7.42–7.38 (m, 2 H), 7.38–7.21 (m, 2 H), 7.07–7.02 (m, 2 H), 6.35 (d, J = 15.5 Hz, 1 H) |
| pyrid-2-yl | 2-chloro-phenyl | mp 204–205° C.<br>NMR δ 8.49–8.47 (m, 1 H), 7.94 (d, J = 15.3 Hz, 1 H), 7.84 (d, J = 4.6 Hz, 1 H), 7.65–7.59 (m, 2 H), 7.53–7.47 (m, 2 H), 7.42–7.37 (m, 2 H), 7.29 (d, J = 7 Hz, 1 H), 7.16–7.13 (m, 1 H), 6.93 (d, J = 15.3 Hz, 1 H) Analysis calculated for $C_{19}H_{12}ClN_3OS$: C, 62.39; H, 3.28; N, 11.49. Found: C, 62.71; H, 3.35; N, 11.45. |
| 2-methoxy-phenyl | 2-chloro-phenyl | mp 90–91° C.<br>NMR δ 8.15 (d, J = 15 6 Hz, 1 H), 7.83 (d, J = 5.3 Hz, 1 H), 7.66–7.63 (m, 1 H), 7.50 (sym m, 2 H), 7.41–7.33 (m, 2 H), 7.29–7.23 (m, 2 H), 6.90–6.82 (m, 2 H), 6.55 (d, J = 15.5 Hz, 1 H), 3.71 (s, 3 H) |
| 4-methoxy-phenyl | 2-chloro-phenyl | mp 88–89° C.<br>NMR δ 7.93 (d, J = 15.4 Hz, 1 H), 7.83 (d, J = 5.2 Hz, 1 H), 7.66–7.63 (m, 1 H), 7.51 (sym m, 2 H), 7.41–7.36 (m, 2 H), 7.27–7.24 (m, 2 H), 6.82 (d, J = 8.8 Hz, 1 H), 6.13 (d, J = 15.4 Hz, 1 H), 3.79 (s, 3H) |
| 4-carbo-methoxy-phenyl | 2-methyl-phenyl | mp 187–188° C.<br>NMR δ 7.98–7.92 (m, 3 H), 7.85 (d, J = 5.2 Hz, 1 H), 7.50–7.38 (m, 4 H), 7.32 (d, J = 8.3 Hz, 2 H), 7.21 (d, J = 7.8 Hz, 1 H), 6.39 (d, J = 15.6 Hz, 1 H), 3.89 (s, 3 H), 2.12 (s, 3 H) |
| 2-hydroxy-phenyl | 2-chloro-phenyl | mp 245° C.<br>NMR δ 8.29 (d, J = 15.5 Hz, 1 H), 7.86 (d, J = 5.3 Hz, 1 H), 7.63–7.59 (m, 1 H), 7.50–7.44 (m, 4 H), 7.39–7.36 (m, 2 H), 7.11 (t, J = 8 Hz, 1 H), 6.81–6.76 (m, 1 H), 6.69 (d, J = 8 Hz, 1 H), 5.95 (d, J = 15.7 Hz, 1 H) |
| pyrid-2-yl | 2-bromo- | mp 221° C. |
| phenyl | | NMR δ 8.48 (d, J = 4.7 Hz, 1 H), 7.95 (d, J = 15 Hz, 1 H), 7.85 (d, H = 5.4 Hz, 1 H), 7.80 (dd, J = 1.4, 8 Hz, 1 H), 7.63 (dt, J = 1.8, 7.7 Hz, 1 H), 7.54 (dt, J = 1.5, 7.5 Hz, 1 H), , 7.46–7.33 (m, 3 H), 7.29 (d, J = 7.9 Hz, 1 H), 7.18–7.14 (m, 1 H), 6.92 (d, J = 15 Hz, 1 H) |
| 2-fluoro-phenyl | 2-chloro-pyrid-3-yl | Isolated as hydrochloride salt.<br>mp 234–236° C.<br>NMR (DMSO d6) δ 8.68 (dd, J = 1.8, 4.8 Hz, 1 H), 8.36 (d, J = 5.3 Hz, 1 H), 8.29 (dd, J = 1.9, 7.8 Hz, 1 H), 7.98 (d, J = 15.6 Hz, 1 H), 7.76 (dd, J = 4.8, 7.8 Hz, 1 H), 7.59 (d, J = 5.2 Hz, 1 H), 7.48–7.38 (m, 1 H), 7.28–7.18 (m, 2 H), 6.49 (d, J = 15.6 Hz, 1 H) |
| 2-methoxy-phenyl | 2-methyl-phenyl | mp 154° C.<br>NMR δ 8.13 (d, J = 15.6 Hz, 1 H), 7.81 (d, J = 5.2 Hz, 1 H), 7.42 (sym m, 4 H), 7.25–7.20 (m, 3 H), 6.89–6.81 (m, 2 H), 6.58 (d, J = 15.5 Hz, 1 H), 3.69 (s, 3 H), 2.11 (s, 3 H) |
| 2-hydroxy-phenyl | 2-methyl-phenyl | mp >256° C.<br>NMR (DMSO d6) δ 8.28 (d, J = 5.4 Hz, 1 H), 8.07 (d, J = 15.7 Hz, 1 H), 7.53 (d, J = 5.3 Hz, 1 H), 7.50–7.36 (m, 4 H), 7.18–7.12 (m, 2 H), 6.84 (d, J = 8 Hz, 1 H), 6.75 (t, J = 7.5 Hz, 1 H), 6.52 (d, J = 5.5 Hz, 1 h), 2.02 (s, 3 H) |
| pyrid-2-yl | 2-chloro-pyrid-3-yl | mp 244° C.<br>NMR δ 8.61 (dd, J = 1.8, 4.8 Hz, 1 H), 8.48 (d, J = 4.3 Hz, 1 H), 7.96 (d, J = 14.8 Hz, 1 H), 7.88 (d, J = 5.2 Hz, 1 H), 7.80 (dd, J = 1.8, 7.8 Hz, 1 H), 7.65 (dt, J = 1.8, 7.7 Hz, 1 H), 7.52 (dd, J = 4.8, 7.8 Hz, 1 H), 7.43 (d, J = 5.2 Hz, 1 H), 7.31 (d, J = 7.8 Hz, 1 H), 7.21–7.16 (m, 1 H), 6.93 (d, J = 14.8 Hz, 1 H) |
| 4-methyl-(1,3)-thiazol-2-yl | 2-methyl-phenyl | mp 198–200° C.<br>NMR δ 7.99 (d, J = 15.2 Hz, 1 H), 7.82 (dd, J = 1.1,5.3 Hz, 1 H), 7.41 (m, 4 H), 7.18 (d, J = 7.5 Hz, 1 H), 6.85 (s, 1 H), 6.59 (d, J = 15.1 Hz, 1 H), 2.39 (s, 3 H), 2.10 (s, 3 H). |
| 2-methyl-thiazol-4-yl | 2-chloro-pyrid-3-yl | mp 206–208° C.<br>NMR δ 8.60 (m, 1 H), 7.90 (d, J = 14.8 Hz, 1 H), 7.86 (dd, J = 0.7, 5.2 Hz, 1 H), 7.78 (m, 1 H), 7.51 (dd, J = 4.8, 7.7 Hz, 1 H), 7.41 (d, J = 5.4 Hz, 1 H), 7.25 (s, 1 H), 6.61 (d, J = 14.7 Hz, 1 H), 2.63 (s, 3 H). |
| 2-methyl-thiazol-4-yl | 2-methyl-pyrid-3-yl | mp 215° C.<br>NMR δ 8.67 (br d, J = 4.2 Hz, 1 H), 7.88–7.83 (m, 2 H), 7.56 (d, J = 7.5 Hz, 1 H), 7.38 (m, 2 H), 7.20 (s, 1 H), 6.57 (d, J = 14.8 Hz, 1 H), 2.59 (s, 3 H), 2.37 (s, 3 H). |
| 2-methyl-1,3-thiazol-4-yl | 2-methyl-phenyl | mp 246–247° C.<br>NMR δ 7.89 (d, J = 15 Hz, 1 H), 7.77 (m, 1 H), 7.43 (m, 4 H), 7.25 (s, 1 H), 7.19 (s, 1 H)1 6.62 (d, J = 14.9 Hz, 1 H), 2.61 (s, 3 H), 2.11 (s 3 H). |

EXAMPLE 5

The compounds in Table 2 were prepared by substantially the same methodology described in Examples 1–3, with the exception of employing the products of preparations 15 and 17 in the reactions.

TABLE 2

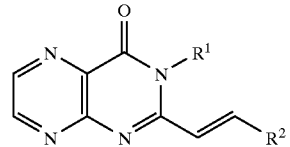

| R² | R¹ | Physical Data |
|---|---|---|
| 2-fluoro-phenyl | 2-methyl-phenyl | mp 195° C.<br>NMR δ 8.31 (d, J = 3.2 Hz, 1 H), 7.94 (d, J = 15.9 Hz, 1 H), 7.62 (d, J = 3.3 Hz, 1 H), 7.43–7.33 (m, 3 H), 7.23–7.16 (m, 3 H), 7.05–6.85 (m, 2 H), 6.38 (d, J = 16.1 Hz, 1 H), 2.12 (s, 3 H)<br>Analysis calculated for $C_{21}H_{15}FN_2OS$: C, 69.61; H, 4.14; N, 7.73. Found: C, 69.11; H, 4.10; N, 7.35. |
| pyrid-2-yl | 2-methyl-phenyl | mp 190–191° C.<br>NMR δ 8.46 (dd, J = 1.6, 4.5 Hz, 1 H), 8.31 (d, J = 3.2 Hz, 1 H), 7.83 (d, J = 15.3 Hz, 1 H), 7.61–7.56 (m, 2 H), 7.42–7.35 (m, 3 H), 7.24–7.11 (m, 3 H), 6.83 (d, J = 15.2 Hz, 1 H), 2.11 (s, 3 H)<br>Analysis calculated for $C_{20}H_{15}N_3OS$: C, 69.57; H, 4.35; N, 12.17. Found: C, 69.16, H, 4.36; N, 11.76. |
| pyrid-2-yl | 2-chloro-phenyl | mp 207° C.<br>NMR δ 8.46 (dd, J = 1.5, 3 Hz, 1 H), 8.31 (d, J = 3.9 Hz, 1 H), 7.83 (d, J = 14.8 Hz, 1 H), 7.62–7.12 (m, 8 H), 6.85 (d, J = 14.8 Hz, 1 H) |

EXAMPLE 6

2-[2-(2-Fluoro-phenyl)-vinyl]-3-o-tolyl-3H-pteridin-4-one

A mixture of fused zinc chloride (0.17 g, 1.25 mmol), dioxane (15 mL), 2-methyl-3-(2-methyl-phenyl)-3H-pteridin-4-one (0.174 g, 0.69 mmol, preparation 8), and 2-fluorobenzaldehyde (0.22 mL, 2.07 mmol), and acetic anhydride 0.195 mL, 2.07 mmol) was refluxed overnight. The reaction was cooled and concentrated. The residual material was partitioned between saturated aqueous sodium bicarbonate and methylene chloride. The layers were carefully shaken and separated. The organic layer was washed with brine, dried and concentrated. The residue was flash chromatographed on silica gel (0.75×4 inches) with elution proceeding as follows: 50% ethyl acetate/hexane (300 mL), forerun; 60% ethyl acetate/hexane (400 mL). 2-[2-(2-Fluoro-phenyl)-vinyl]-3-o-tolyl-3H-pteridin-4-one (0.137 g, 55%) was isolated as a yellow crystalline solid. A sample was recrystallized from ethyl acetate.

Mp >250° C.; NMR δ8.98 (d, J=2 Hz, 1H), 8.80 (d, J=2 Hz, 1H), 8.36 (d, J=15.5 Hz, 1H), 7.54–7.40 (m, 3H), 7.35–7.20 (m, 3H), 7.15–6.98 (m, 2H), 6.49 (d, J=15 Hz, 1H), 2.15 (s, 3H). Analysis calculated for $C_{21}H_{15}FN_4O$: C, 70.38; H, 4.22; N, 15.63. Found: C, 70.07; H, 4.21; N, 15.78.

EXAMPLE 7

The compounds in Table 3 were prepared following substantially the same procedure as found in Example 6 starting with the product of either preparation 8 or preparation 11.

TABLE 3

| R² | R¹ | Physical Data |
|---|---|---|
| pyrid-2-yl | 2-methyl-phenyl | mp >250° C.<br>NMR δ 9.00 (d, J = 2 Hz, 1 H), 8.83 (d, J = 2 Hz, 1 H), 8.51 (long range coupled d, J = 3.5 Hz, 1 H), 8.29 (d, J = 15 Hz, 1 H), 7.68 (dt, J = 2, 7.5 Hz, 1 H), 7.56–7.40 (m, 3 H), 7.35 (d, J = 7.5 Hz, 1 H), 7.26–7.18 (m, 2 H), 7.01 (d, J = 15 Hz, 1 H), 2.18 (s, 3 H)<br>Analysis calculated for $C_{20}H_{15}N_5O$: C, 70.37; H, 4.43; N, 20.52. Found: C, 69.97; H, 4.43; N, 20.78. |
| 2-fluoro-phenyl | 2-chloro-phenyl | mp 228–230° C.<br>NMR δ 8.98 (d, J = 2 Hz, 1 H), 8.81 (d, J = 2 Hz, 1 H), 8.35 (d, J = 15.5 Hz, 1 H), 7.71–7.63 (m, 1 H), 7.55 (sym m, 2 H), 7.48–7.40 (m, 1 H), 7.37–7.25 (m, 2 H), 7.13–6.95 (m, 2 H), 6.47 (dd, J = 1, 15.5 Hz, 1 H).<br>Analysis calculated for $C_{20}H_{12}ClFN_4O \cdot 0.5 H_2O$: C, 61.94; H, 3.38; N, 14.45. Found: C, 62.17; H, 3.32; N, 14.54. |
| pyrid-2-yl | 2-chloro-phenyl | mp 231–232° C.<br>NMR δ 8.98 (d, J = 2 Hz, 1 H), 8.81 (d, J = 2 Hz, 1 H), 8.51–8.48 (sym m, 1 H), 8.28 (d, J = 15 Hz, 1 H), 7.72–7.62 (m, 2 H), 7.55 (sym m, 2 H), 7.48–7.40 (m, 1 H), 7.34 (d, J = 7.5 Hz, 1 H), 7.19 (sym m, 1 H), 6.98 (d, J = 15 Hz, 1 H)<br>Analysis calculated for $C_{19}H_{12}ClN_5O \cdot 0.5 H_2O$: C, 61.55; H, 3.53; N, 18.89. Found: C, 61.67; H, 3.38; N, 19.13. |

EXAMPLE 8

2-[2-(2-Fluoro-phenyl)-vinyl]-3-o-tolyl-3H-pyrido[3,4-d]pyrimidin-4-one

The title compound was prepared according to the procedures of Examples 1–3 from the product of preparation 20.

Mp 211–211.5° C.; NMR δ9.26 (s, 1H), 8.70 (d, J=5 Hz, 1 h), 8.18 (d, J=15.5 Hz, 1H), 8.08 (d, J=4.5 Hz, 1H), 7.54–7.48 (m, 3 h), 7.46–7.15 (m, 3H), 7.13–7.00 (m, 2 h), 6.47 (d, J=15.5 Hz, 1H), 2.13 (s, 3H). Analysis calculated for $C_{22}H_{16}FN_3 \cdot 0.125 H_2O$: C, 73.47; H, 4.55; N, 11.68. Found: C, 73.35; H, 4.49; N, 11.66.

EXAMPLE 9

3-(2-Chloro-phenyl)-2-(2-pyridin-2-yl-ethyl)-3H-thieno[3,2-d]pyrimidin-4-one Hydrochloride A mixture of 3-(2-chloro-phenyl)-2-[2-pyrid-2-yl-vinyl]-3H-thieno[3,2-d]pyrimidin-4-one (0.12 g, 0.33 mmol), ethanol, 10 mL), formic acid (0.55 mL, 14.8 mmol) and 10% palladium on carbon (0.12 g) was refluxed 4 hours, cooled and diluted with ethanol and water. The mixture was filtered through Celite® (trademark) and the pad was rinsed with ethyl acetate and water. The filtrate was treated with saturated aqueous sodium bicarbonate and the phases were separated. The aqueous layer was extracted with ethyl acetate and the combined organic phase was washed with water and brine, dried over sodium sulfate, and concentrated to afford 0.094 g of 3-(2-chloro-phenyl)-2-(2-pyridin-2-yl-ethyl)-3H-thieno[3,2-d]pyrimidin-4-one as a tan film. The material was dissolved in dioxane (3 mL) and treated with ether saturated with hydrogen chloride. The solid was collected and weighed 0.094 g. The solid was taken up in water, concentrated, and azeotropically dried by suspending the product in chloroform and concentrating three times to yield 3-(2-chloro-phenyl)-2-(2-pyridin-2-yl-ethyl)-3H-thieno[3,2-d]pyrimidin-4-one hydrochloride (0.038 g, 31%) as a yellow solid.

Mp 136° C. Analysis calculated for $C_{19}H_{14}ClN_3OS$ HCl 1.5 $H_2O$: C, 52.13; H, 4.11; N, 9.15. Found: C, 51.96; H, 3.78; N, 9.27.

EXAMPLE 10

The compounds in Table 4 were prepared following the procedure of Example 9.

TABLE 4

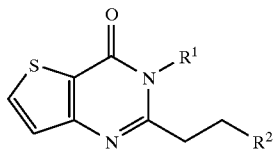

| $R^2$ | $R^1$ | Physical Data |
|---|---|---|
| 2-fluoro-phenyl | 2-methyl-phenyl | mp 168° C. NMR δ 7.80 (d, J = 5.3 Hz, 1 H), 7.38–7.31 (m, 4 H), 7.05–6.92 (m, 6 H), 3.07 (t, J = 7.9 Hz, 2 H), 2.62 (sym m, 2 H), 2.04 (s, 3 H) MS m/e = 364 |
| pyrid-2-yl | 2-methyl-phenyl | mp 190–191° C. NMR δ 8.41 (d, J = 4.3 Hz, 1 H), 7.75 (d, J = 5.3 Hz, 1 H), 7.49 (dt, J = 1.6, 7.6 Hz, 1 H), 7.36–7.24 (m, 4 H), 7.12–7.00 (m, 3 H), 3.27–3.21 (m, 2 H), 2.83–2.73 (m, 2 H), 2.05 (s, 3 H) |
| 4-methyl-1,3-thiazol-2-yl | 2-methyl-phenyl | isolated as a foam NMR δ 7.78 (d, J = 5.4 Hz, 1 H), 7.34 (m, 4 H), 7.07 (d, J = 7.3 Hz, 1 H), 6.64 (s, 1 H), 3.44 (sym m, 2 H), 2.83 (m, 1 H), 2.67 (m, 1 H), 2.33 (s, 3 H), 2.05 (s, 3 H). The HCl salt was precipitated from 1 N ethereal HCl and had: mp 146–150° C. |
| 2-methyl-1,3-thiazol-4-yl | 2-methyl-phenyl | Isolated as a yellow film NMR δ 7.79 (dd, J = 1.2, 5.3 Hz, 1 H), 7.36 (m, 4 H), 7.05 (d, J = 7.4 Hz, 1 H), 6.67 (s, 1 H), 3.18 (t with incompletely resolved fine coupling, J = 8.1 Hz, 2 H), 2.74 (m, 1 H), 2.65 (m, 1 H), 2.60 (s, 3 H), 2.03 (s, 3 H). The HCl salt was precipitated from 1 N ethereal HCl and had: mp 127–129° C. |

EXAMPLE 11

The compounds in Table 5 were prepared following the procedure of Example 9.

TABLE 5

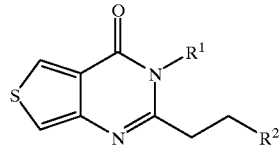

| $R^2$ | $R^1$ | Physical Data |
|---|---|---|
| pyrid-2-yl | 2-methyl-phenyl | Hydrochloride mp 162° C. NMR (DMSO d6) δ 8.76 (d, J = 4.9 Hz, 1 H), 8.54 (d, J = 3.2 Hz, 1 H), 8.45 (dt, J = 1.5, 8 Hz, 1 H), 7.96 (d, J = 7.9 Hz, 1 H), 7.85 (t, J = 7 Hz, 1 H), 7.81 (d, J = 3.2 Hz, 1 H), 7.44–7.37 (m, 4 H), 3.42 (t, J = 6.9 Hz, 2 H), 2.86 (dt, J = 6.8, 18 Hz, 1 H), 2.60 (dt, J = 6.8, 18 Hz, 1 H), 2.03 (s, 3 H) Analysis calculated for $C_{20}H_{17}N_3OS.HCl.H_2O$: C, 59.85; H, 4.90; N, 10.00. Found: C, 59.58; H, 4.99; N, 9.88. |
| pyrid-2-yl | 2-chloro-phenyl | Hydrochloride mp 181–183° C. NMR (DMSO d6) δ 8.77 (d, J = 4.8 Hz, 1 H), 8.57 (d, J = 3.2 Hz, 1 H), 8.46 (dt, J = 1.5, 8 Hz, 1 H), 7.98 (d, J = 8 Hz, 1 H), 7.86 (t, J = 6.5 Hz, 1 H), 7.76–7.68 (m, 2 H), 7.60–7.56 (m, 2 H), 3.45 (t, J = 7 Hz, 2 H), 2.93 (dt, J = 6.7, 18 Hz, 1 H), 2.63 (dt, J = 6.7, 18 Hz, 1 H) Analysis calculated for $C_{19}H_{14}ClN_3OS.HCl.1.5 H_2O$: C, 53.46; H, 4.10; N, 9.85. Found: C, 53.64; H, 3.95; N, 9.48. |

EXAMPLE 12

5-(2-Pyridin-2-yl-vinyl)-6-o-tolyl-3,6-dihydro-[1,2,3]triazolo[4,5-d]pyrimidin-7-one To a mixture of fused zinc chloride (0.551 g, 4.04 mmol) and dioxane (20 mL) was added 5-methyl-6-o-tolyl-3,6-dihydro-[1,2,3]triazolo[4,5-d]pyrimidin-7-one (0.488 g, 2.02 mmol), 2-pyridinecarboxaldehyde (0.58 mL, 6.06 mmol), and acetic anhydride (0.57 mL, 6.06 mmol). The mixture was heated to 70° C. for 6 hours, cooled, and quenched with saturated sodium bicarbonate. This mixture was stirred overnight at ambient temperature. The dioxane was removed at reduced pressure and the resulting black liquid was extracted with methylene chloride. The organic phase was dried over magnesium sulfate, treated with activated carbon, filtered, and concentrated. The residue (1.5 g) was flash chromatographed on silica gel (50 g). Elution with 50% and 60% ethyl acetate/hexane gave 5-(2-pyridin-2-yl-vinyl)-6-o-tolyl-3,6-dihydro-[1,2,3]triazolo[4,5-d]pyrimidin-7-one (0.023 g, 3.5%).

NMR δ9.06 (d, J=7.3 Hz, 1H), 8.70 (m, 2H), 7.60 (t, J=7.8 Hz, 1H), 7.50 (t, J=7.7 Hz, 1H), 7.32–7.00 (m, 4H), 6.80 (t, J=8.2 Hz, 1H), 6.59 (t, J=8 Hz, 1H), 2.28 (s, 3H); MS m/e=330. The product was treated with hydrogen chloride (HCl) in dioxane to form the hydrochloride salt which had a melting point (mp) of 80–85° C.

Preparation 1

3-Acetamidothiophene-2-carboxylic acid

To a solution of methyl 3-aminothiophene-2-carboxylate (10 g, 0.0637 mol) and triethylamine (10.3 g, 0.102 mol) in methylene chloride was added acetyl chloride (8.0 g, 0.102 mol in 10 mL of methylene chloride), dropwise. The reaction was stirred 3 hours at ambient temperature. The mixture was quenched with water and the phases were separated. The aqueous layer was extracted twice with methylene chloride and the combined organic phase was washed with water and brine, dried over sodium sulfate and concentrated to afford 14.0 g of yellow solid product which was suitable for reaction without further purification.

NMR δ8.10 (d, J=5.4 Hz, 1H), 7.43 (d,J=5.4 Hz, 1H), 3.86 (s, 1H), 2.20 (s, 3H); MS m/e=199.

The product was added to 200 mL of 10% methanolic potassium hydroxide and heated to 60–65° C. for 4 hours. The reaction was concentrated and the residue taken up in water. The aqueous solution was extracted with ether and then made acidic with 6 N hydrochloric acid (HCl). The precipitate was filtered, washed well with water, and air dried to yield 9.5 g (80%) of 3-acetamidothiophene-2-carboxylic acid as a tan solid.

Mp 212–213° C.; NMR (DMSO d6) δ7.82 (d, J=5.4 Hz, 1H), 7.72 (d, J=5.4 Hz, 1H), 2.06 (s, 3H).

Preparation 2

2-Methyl-3-(2-methylphenyl)-3H-thieno[3,2-d] pyrimidin-4-one

To a mixture of 3-acetamidothiophene-2-carboxylic acid (15.1 g, 75.67 mmol) and sodium acetate (6.45 g, 78.6 mmol) in dioxane (200 mL) was added acetic anhydride (71 mL, 75.7 mmol). The reaction was refluxed 2 hours, cooled to ambient temperature and partitioned between chloroform and water. Phases were separated and the aqueous layer was extracted with chloroform. The combined organic phase was washed with water and brine, dried over magnesiuym sulfate and concentrated to leave 15.1 g of 2-methyl-thieno[3,2-d] [1,3]oxazin-4-one as a brown oil which slowly solidified.

NMR δ7.78 (d, J=6.5 Hz, 1H), 7.14 (d, J=6.5 Hz, 1H), 2.40 (s, 3H); MS m/e=167. The material was used without further purification.

2-Methyl-thieno[3,2-d][1,3]oxazin4-one (12.7 g, 76 mmol) and o-toluidine (16.2 mL, 152 mmol) were combined in acetic acid (175 mL) and refluxed for 3 hours. The reaction was concentrated and the residue was partitioned between ethyl acetate and water. The two phase mixture was treated with sodium bicarbonate until the aqueous layer was basic and the phases were then separated. The aqueous phase was extracted with ethyl acetate and the combined organic layer was washed with water and brine, dried over sodium sulfate and concentrated to leave a black oil. This residue was purified by flash chromatography on silica gel (60×200 mm). Elution with 20% ethyl acetate/hexane gave 16.2 g of impure product and 3 g of uncyclized diamide biproduct. The impure product was chromatographed a second time as above but with 10% and 15% ethyl acetate/hexane elution. In this fashion 9.2 g (47%) of 2-methyl-3-(2-methylphenyl)-3H-thieno[3,2-d]pyrimidin-4-one was isolated as a light yellow solid. NMR δ7.70 (d, J=5.3 Hz, 1H), 7.39–7.30 (m, 3H), 7.29 (d, J=5.3 Hz, 1H), 7.13 (d, J=7.8 Hz, 1H), 2.15 (s, 3H), 2.10 (s, 3H).

Preparation 3

2-Methyl-3-(2-chlorophenyl)-3H-thieno[3,2-d] pyrimidin-4-one

2-Methyl-thieno[3,2-d][1,3]oxazin-4-one (1.67 g, 10 mmol) and o-chloroaniline (2.1 mL, 20 mmol) were combined in acetic acid (20 mL) and refluxed for 4.5 hours. The reaction was partitioned between ethyl acetate and water. The two phase mixture was treated with sodium bicarbonate until the aqueous layer was basic and the phases were then separated. The aqueous phase was extracted with ethyl acetate and the combined organic layer was washed with water and brine, dried over sodium sulfate and concentrated to leave a brown oil. This residue was purified by flash chromatography on silica gel (30×150 mm). Elution with 10% and 20% ethyl acetate/hexane gave 1.42 g (51%) of 2-methyl-3-(2-chlorophenyl)-3H-thieno[3,2-d]pyrimidin-4-one was isolated as a brown oil which solidified on standing.

MP 118–121° C.; NMR δ7.78 (d, J=5.3 Hz, 1H), 7.57 (m, 1 H), 7.46–7.43 (m, 2H), 7.33–7.29 (m, 2H), 2.20 (s, 3H); MS m/e=276.

Preparation 4

2-Methyl-3-(2-chloropyrid-3-yl)-3H-thieno[3,2-d] pyrimidin-4-one

To a mixture of pyridine (4 mL), 3-amino-2-chloropyridine (0.514 g, 4 mmol), and 3-acetamidothiophene-2-carboxylic acid (0.370 g, 4 mmol) was added phosphorus trichloride (0.02 mL, 2.3 mmol). The reaction was heated to 105° C. for 3 hours, cooled to ambient temperature and partitioned between ethyl acetate and water. Phases were separated and the aqueous layer was extracted with ethyl acetate. The combined organic phase was washed with water and brine, dried over sodium sulfate and concentrated to a greenish brown oil. This residue was flash chromatographed on silica gel (20×120 mm) eluting with 20–40% ethyl acetate/hexane to afford 0.350 g (63%) of 2-methyl-3-(2-chloropyrid-3-yl)-3H-thieno[3,2-d] pyrimidin-4-one as a yellow foam.

NMR 678.58–8.56 (m, 1H), 7.83 (d, J=5.2 Hz, 1H), 7.74–7.71 (m, 1 H), 7.50–7.46 (m, 1H), 7.33 (d, J=5.3 Hz, 1H), 2.24 (s, 3H); MS m/e=277.

Preparation 5

2-Methyl-3-(2-bromophenyl)-3H-thieno[3,2-d] pyrimidin-4-one

To a mixture of pyridine (6 mL), 2-bromoaniline (1.03 g, 6 mmol), and 3-acetamidothiophene-2-carboxylic acid (0.555 g, 3 mmol) was added phosphorus trichloride (0.03 mL, 3.45 mmol). The reaction was heated to 105° C. for 4 hours, cooled to ambient temperature and partitioned between chloroform and water (an insoluble precipitate was removed by filtration). Phases were separated and the aqueous layer was extracted with chloroform. The combined organic phase was washed with water and brine, dried over magnesium sulfate and concentrated to a dull yellow film. This residue was flash chromatographed on silica gel (30× 125 mm) eluting with 15–25% ethyl acetate/hexane to afford 0.411 g (47%) of 2-methyl-3-(2-bromophenyl)-3H-thieno[3, 2-d]pyrimidin-4-one as a yellow foam.

NMR δ7.76–7.55 (m, 2H), 7.44 (t, J=7.2 Hz, 1H), 7.39–7.05 (m, 3H), 2.10 (s, 3H); MS m/e=320 and 322.

Preparation 6

3-Aminopyrazine-2-carboxylic acid o-toluamide

A mixture of 3-aminopyrazine carboxylic acid (5.0 g, 35.94 mmol), methylene chloride (110 mL), 4-dimethylaminopyridine (10.98 g, 89.85 mmol), o-toluidine (4.22 mL, 39.53 mmol), and 1-(3-dimethylaminopropyl)-3-ethylcarbodiimide hydrochloride (8.27 g, 43.13 mmol) was stirred overnight at ambient temperature. The solvent was removed and the residue was diluted with ethyl acetate. This organic phase was extracted with 1 N lithium chloride (LiCl), water, and brine, dried over calcium sulfate and concentrated. The residue was flash chromatographed on silica gel (2.75×4 inches) with elution proceeding as follows: hexane (300 mL), nil; 20% ethyl acetate/hexane (500 mL), unweighed recovered o-toluidine; 20% ethyl acetate/hexane (1000 mL) and 30% ethyl acetate/hexane (2000 mL), 4.79 g (58%) of 3-aminopyrazine-2-carboxylic acid o-toluamide as a yellow crystalline solid.

Mp 135–137° C.; NMR δ9.80 (br s, 1H), 8.22 (d, J=2.5 Hz, 1H), 8.11 (d, J=8.0 Hz, 1H), 7.87 (d, J=2.5 Hz, 1H), 7.33–7.23 (m, 2H), 7.10 (dt, J=1, 7.5 Hz, 1), 2.39 (s, 3H).

Preparation 7

3-Acetamidopyrazine-2-carboxylic acid o-toluamide

A mixture of 3-aminopyrazine-2-carboxylic acid o-toluamide (1.0 g, 4.39 mmol) and acetic anhydride (12 mL) was refluxed 2 hours. The solvent was removed and the residue was triturated with hot ethyl acetate. The ethyl acetate slurry was cooled and the product was collected and rinsed with ether to afford 0.893 g (76%) of 3-acetamidopyrazine-2-carboxylic acid o-toluamide.

NMR δ11.88 (br s, 1H), 10.0 (br s, 1H), 8.65 (d, J=2.5 Hz, 1H), 8.28 (d, J=2.5 Hz, 1H), 8.04 (d, J=8 Hz, 1H), 7.38–7.24 (m, 2 H), 7.20–7.11 (m, 1), 2.39 (s, 3H), 2.38 (s, 3H). The material was used without further purification.

Preparation 8

2-Methyl-3-(2-methyl-phenyl)-3H-pteridin-4-one

To a mixture of 3-acetamidopyrazine-2-carboxylic acid o-toluamide (1.0 g, 3.70 mmol), triphenylphosphine (2.91 g, 11.1 mmol), and 4-dimethylaminopyridine (0.045 g, about 10 mol %) in dioxane (45 mL) was added diethyl azodicarboxylate (1.75 mL, 11.1 mmol) dropwise via syringe. The reaction was refluxed overnight, cooled to ambient temperature and concentrated. The residue was partitioned between methylene chloride and water. The phases were separated and the organic layer was washed with brine, dried and concentrated. The residue was flash chromatographed on silica gel (2.25×4 inches, packed in hexane) with elution proceeding as follows: 20%–80% ethyl acetate/hexane, forerun; 85% ethyl acetate/hexane (1000 mL), 0.71 g (76%) of 2-methyl-3-(2-methyl-phenyl)-3H-pteridin-4-one which was suitable for use without further purification. A sample was recrystallized from ethyl acetate.

Mp 186–187° C.; NMR δ8.98 (d, J=2 Hz, 1H), 8.83 (d, J=2 Hz, 1H), 7.51–7.35 (m, 3H), 7.18 (d, J=7 Hz, 1H), 2.30 (s, 3H), 2.16 (s, 3H).

Preparation 9

3-Aminopyrazine-2-carboxylic acid 2-chlorophenylamide

A mixture of 3-aminopyrazine carboxylic acid (7.0 g, 50.32 mmol), methylene chloride (60 mL), dimethylformamide (40 mL), 4-dimethylaminopyridine (15.37 g, 126 mmol), 2-chloroaniline (5.82 mL, 55.35 mmol), and 1-(3-dimethylaminopropyl)-3-ethylcarbodiimide hydrochloride (11.58 g, 60.38 mmol) was stirred overnight at ambient temperature. The solvent was removed and the residue was mixed with ethyl acetate and 1 N lithium chloride. The precipitate which formed was filtered and rinsed with 1 N lithium chloride, ethyl acetate, and ether and then air dried to afford 6.22 g (50%) of 3-aminopyrazine-2-carboxylic acid 2-chlorophenylamide as fluffy yellow crystals.

Mp 177–179° C.; NMR δ10.47 (br s, 1H), 8.52 (dd, J=1.5, 8.5 Hz, 1H), 8.23 (d, J=2.5 Hz, 1H), 7.92 (d, J=2.5 Hz, 1H), 7.43 (dd, J=1.5, 8 Hz, 1H), 7.33 (dt, J=1.5, 7.5 Hz, 1H), 7.09 (dt, J=1.5, 7.5 Hz, 1H).

Preparation 10

3-Acetamidopyrazine-2-carboxylic acid 2-chlorophenylamide

A mixture of 3-aminopyrazine-2-carboxylic acid 2-chlorophenyl (4.0 g, 16.1 mmol) and acetic anhydride (25 mL) was refluxed for 2 hours. The solvent was removed and the residue was partitioned between methylene chloride and saturated aqueous sodium bicarbonate. The phases were separated and the organic layer was washed with brine, dried and concentrated. The residue was flash chromatographed on silica gel (2.25×4 inches) with elution proceeding as follows: hexane (200 mL) and 25% ethyl acetate/hexane (500 mL), forerun; 40% ethyl acetate/hexane (700 mL, 0.69 g of an unidentified material; 40% ethyl acetate/hexane (200 mL) and 60% ethyl acetate/hexane (500 mL), 0.836 g (18%) of 3-acetamidopyrazine-2-carboxylic acid 2-chlorophenylamide.

Mp 194–196° C.; NMR δ11.70 (br s, 1H), 10.65 (br s, 1H), 8.66 (d, J=2.5 Hz, 1H), 8.49 (dd, J 1.5, 8 Hz, 1H), 8.31 (d, J=2.5 Hz, 1H), 7.46 (dd, J=1.5, 10 Hz, 1H), 7.36 (dt, J=1.5, 9 Hz, 1H), 7.14 (dt, J=1.5, 7.5 Hz, 1H), 2.42 (s, 3H). The material was used without further purification.

Preparation 11

2-Methyl-3-(2-chloro-phenyl)-3H-pteridin-4-one

To a mixture of 3-acetamidopyrazine-2-carboxylic acid 2-chlorophenylamide (0.816 g, 2.81 mmol), triphenylphosphine (2.21 g, 8.43 mmol), and 4-dimethylaminopyridine (0.034 g, 0.28 mmol) in dioxane (35 mL) was added diethyl azodicarboxylate (1.33 mL, 8.43 mmol), dropwise via syringe. The reaction was refluxed overnight, cooled to ambient temperature and concentrated. The residue was partitioned between methylene chloride and water. The phases were separated and the organic layer was washed with brine, dried and concentrated. The residue was flash chromatographed on silica gel (1.5×5 inches, packed in hexane) with elution proceeding as follows: 20% ethyl acetate/hexane (250 mL), forerun; 40% ethyl acetate/hexane (1600 mL), unweighed triphenylphosphine oxide; 60% ethyl acetate/hexane (500 mL) and 75% ethyl acetate/hexane (500 mL), nil; 80% ethyl acetate/hexane (1000 mL), 0.62 g (81%) of 2-methyl-3-(2-chloro-phenyl)-3H-pteridin-4-one as a brown foam which was suitable for use without further purification. A sample was triturated with hexane.

MP 74–80° C.; NMR δ8.98 (d, J=2 Hz, 1H), 8.84 (d, J=2 Hz, 1H), 7.70–7.63 (m, 1H), 7.53 (sym m, 2H), 7.42–7.33 (m, 1H), 2.34 (s, 3H).

Preparation 12

Methyl 3-acetamidothiophene-4-carboxylate

A mixture of methyl 3-aminothiophene-4-carboxylate hydrochloride (3.1 g, 16 mmol) and triethylamine (6.7 mL, 48 mmol), in methylene chloride (75 mL) was stirred 30 minutes and then chilled over wet ice. Acetyl chloride (1.4 mL, 19.2 mmol) was added and the reaction was warmed to ambient temperature and stirred 1 hour. The reaction was quenched with water and diluted with methylene chloride. The phases were separated and the aqueous layer was extracted with methylene chloride. The combined organic layer was washed with water, dried over magnesium sulfate, and concentrated to afford 2.85 g (91%) of methyl 3-acetamidothiophene-4-carboxylate as a brown oil which solidified on standing. The product was suitable for use without purification.

NMR δ 7.98 (d, 2H), 3.87 (s, 3H), 2.18 (s, 3H).

Preparation 13

3-Acetamidothiophene-4-carboxylic acid

Methyl 3-acetamidothiophene-4-carboxylate (10.0 g, 50.25 mmol) was added to a 5% methanolic potassium hydroxide solution (100 mL). The mixture was refluxed 2 hours, cooled, and concentrated. The residue was dissolved in water and the acidity was adjusted to pH 1 by addition of 1 N hydrochloric acid (HCl). The precipitate was collected, washed with water, and air dried to afford 8.66 g (93%) of 3-acetamidothiophene-4-carboxylic acid.

Mp 206° C.; NMR δ8.29 (d, 1H), 7.88 (d, 1H), 2.11 (s, 3H). The product was used without purification.

Preparation 14

2-Methyl-thieno[3,4-d][1,3]oxazin-4-one

A mixture of 3-acetamidothiophene-4-carboxylic acid (1.6 g, 8.65 mmol), dioxane (40 mL), acetic anhydride (10.2 mL, 86.5 mmol), and sodium acetate (0.75 g, 9.08 mmol) was refluxed overnight. The reaction was cooled and concentrated. The residue was partitioned between ethyl acetate and water. Phases were separated and the aqueous layer was extracted with ethyl acetate. The combined organic layer was washed with water and brine, dried over sodium sulfate, and concentrated to afford 1.39 g (96%) of 2-methyl-thieno[3,4-d][1,3]oxazin-4-one as a tan solid.

NMR δ8.34 (d, J=3.4 Hz, 1H), 7.40 D, J=3.4 Hz, 1H), 2.38 (s, 3H). The product was suitable for use without purification.

Preparation 15

2-Methyl-3-o-tolyl-3H-thieno[3,4-d]pyrimidin-4-one

To a slurry of 2-methyl-thieno[3,4-d][1,3]oxazin-4-one (1.0 g, 5.99 mmol) and acetic acid (15 mL) was added o-toluidine (1.2 mL, 10.78 mmol). The mixture was refluxed 3 hours, cooled, and concentrated. The residue was partitioned between ethyl acetate and water and the aqueous phase was made basic by careful addition of saturated aqueous sodium bicarbonate. The phases were separated and the aqueous layer was extracted with ethyl acetate. The combined organic layer was washed with water and brine, dried over sodium sulfate and concentrated to a black oil. The oil was flash chromatographed on silica gel (30×100 mm) eluting with 20% ethyl acetate/hexane. Product fractions were combined to afford 0.303 g of 2-methyl-3-o-tolyl-3H-thieno[3,4-d]pyrimidin-4-one as a tan oil which solidified on standing.

Mp 122–123° C.; NMR δ78.25 (d, J=3.2 Hz, 1H), 7.47 (d, J=3.3 Hz, 1H), 7.37–7.32 (m, 3H), 7.12 (d, J=6.8 Hz, 1H), 2.13 (s, 3H), 2.10 (s, 3H).

Mixed fractions were chromatographed a second time. Product fractions from this purification were combined, concentrated and the residues were triturated with 10% ethyl acetate/hexane to afford an additional 0.447 g of product. In this fashion 0.75 g (49%) of product was obtained. Later fractions from the chromatography contained uncyclized diamide by product which could be cyclized according the procedure of preparation 17.

Preparation 16

3-Acetamidothiophene-4-carboxylic acid 2-chlorophenylamide

To a slurry of 2-methyl-thieno[3,4-d][1,3]oxazin-4-one (1.3 g, 7.78 mmol) and acetic acid (15 mL) was added 2-chloroaniline (1.64 mL, 15.57 mmol). The mixture was refluxed 4 hours, cooled, and concentrated. The residue was partitioned between ethyl acetate and water and the aqueous phase was made basic by careful addition of saturated aqueous sodium bicarbonate. The phases were separated and the aqueous layer was extracted with ethyl acetate. The combined organic layer was washed with water and brine, dried over sodium sulfate and concentrated to a black oil. The oil was flash chromatographed on silica gel (30×100 mm) eluting with 10% ethyl acetate/hexane. The first component eluting from the column, 0.363 g of white solid was identified as 3-acetamidothiophene-4-carboxylic acid 2-chlorophenylamide.

NMR δ8.33 (d, J=9.7 Hz, 1H), 8.28 (d, J=3.4 Hz, 1H), 8.23 (br s, 1H), 7.78 (d, J=3.3 Hz, 1H), 7.44–7.41 (m, 1 h), 7.30–7.24 (m, 1H), 7.14–7.11(m, 1H), 2.19 (s, 3H); MS m/e=294.

Continued elution gave 0.273 g of an unidentified white solid which had NMR δ78.36 (d, J=8.3 Hz, 1 h), 7.56 (br s, 1 h), 7.35–7.33 (m, 1 h), 7.28–7.22 (m, 1H), 7.04–6.99 (m, 1H), 2.22 (s, 3H).

Preparation 17

2-Methyl-3-(2-chloro-phenyl)-3H-thieno[3,4-d]pyrimidin-4-one

A mixture of 3-acetamidothiophene-4-carboxylic acid 2-chlorophenylamide (0.36 g, 1.23 mmol), toluene (15 mL), and phosphorous oxychloride (0.35 mL, 3.7 mmol) was refluxed 8 hours with azeotropic removal of water (Dean-Stark apparatus). The reaction was cooled and partitioned between ethyl acetate and water. The phases were separated and the aqueous layer was extracted with ethyl acetate. The combined organic layer was washed with water and brine, dried over sodium sulfate, and concentrated. The residue was flash chromatographed on silica gel (20×85 mm) eluting with 10% ethyl acetate/hexane. After an unweighed forerun, 2-methyl-3-(2-chloro-phenyl)-3H-thieno[3,4-d]pyrimidin-4-one was isolated as an off white solid.

NMR δ8.28–8.26 (m, 1H), 7.56–7.55 (m, 1H), 7.49–7.40 (m, 3H), 7.31 (m, 1H), 2.10 (s, 3H); MS m/e=277.

Preparation 18

3-Aminopyridine-4-carboxylic acid

To an ice cold mixture of 3,4-pyridinedicarboximide (5.2 g, 35.11 mmol) in 10% sodium hydroxide (85 mL) was added bromine (1.84 mL, 35.8 mmol), dropwise. The resulting solution was heated to 80° C. for 1 hour, cooled on ice, and the acidity was carefully adjusted to pH 5.5 with acetic acid. The precipitate was collected, washed well with water and air dried to afford 3-aminopyridine-4-carboxylic acid (2.74 g, 57%).

NMR (DMSO d6) δ8.20 (s, 1H), 7.72 (d, J=5 Hz, 1H), 7.45 (d, J=5 Hz, 1H). The material was used without purification.

Preparation 19

2-Methyl-3-oxa-1,7-diaza-naphthalen-4-one

A mixture of 3-aminopyridine-4-carboxylic acid (3.38 g, 24.5 mmol), acetic anhydride (15 mL), and sulfuric acid (3 drops) was refluxed 4 hours. The reaction was cooled and carefully quenched with solid sodium bicarbonate. The mixture was filtered through Celite® (trademark). The filtrate was extracted with ethyl acetate. This organic phase was washed with brine, dried over magnesium sulfate and concentrated to give 2-methyl-3-oxa-1,7-diaza-naphthalen-4-one (1.95 g, 49%) as a brown crystalline material.

NMR δ9.00 (s, 1H), 8.78 (d, J=5 Hz, 1H), 7.96 (d, J=5 Hz, 1H), 2.52 (s, 3H). The product was suitable for use without further purification.

Preparation 20

2-Methyl-3-o-tolyl-3H-pyrido[3,4-d]pyrimidin-4-one

2-Methyl-3-oxa-1,7-diaza-naphthalen-4-one (1.95 g, 12.0 mmol) was dissolved in acetic acid (30 mL) and o-toluidine (1.92 mL, 18 mmol) was added. The reaction was refluxed 7 hours, cooled and concentrated. The residue was taken up in ethyl acetate and extracted with water, saturated aqueous sodium bicarbonate, and brine. The organic layer was dried over magnesium sulfate and concentrated. The residue was flash chromatographed on silica gel (2×4 inches, packed in hexane) with elution proceeding as follows: 10% ethyl acetate/hexane (500 mL); 25% ethyl acetate/hexane (800 mL); 25% ethyl acetate/hexane (200 mL) and 40% ethyl acetate/hexane (200 mL), unweighed recovered 2-methyl-3-oxa-1,7-diaza-naphthalen-4-one; 40% ethyl acetate/hexane (300 mL), unweighed mixed fraction; 40% ethyl acetate/hexane (3000 mL), 2-methyl-3-o-tolyl-3H-pyrido[3,4-d]pyrimidin-4-one (2.47 g, 81%) of as an off white solid.

NMR δ9.15 (s, 1 h), 8.70 (d, J=5 Hz, 1H), 8.05 (d, J=5 Hz, 1H), 7.46–7.35 (m, 3H), 7.16 (d, J=7 Hz, 1 h), 2.23 (s, 3 h), 2.13 (s, 3H). This product was suita for use without further purification.

Preparation 21

Cyanoacetic acid o-toluamide

A mixture of o-toluidine (5.0 mL, 47 mmol), methylene chloride (15 mL), cyanoacetic acid (8.0 g, 94 mmol), 1-hydroxybenzotriazole (12.7 g, 94 mmol), 4-dimethylaminopyridine (5 crystals, catalytic amount), and 1-(3-dimethylaminopropyl)-3-ethylcarbodiimide hydrochloride (16.2 g, 94 mmol) was stirred at ambient temperature overnight. The reaction was concentrated and the residual pale yellow oil was partitioned between ethyl acetate and water. The phases were separated and the organic layer was washed with saturated sodium bicarbonate and brine, dried over sodium sulfate, and concentrated to 5.2 g of off-white solid. This solid was recrystallized from methylene chloride in two crops to afford cyanoacetic acid o-toluamide (4.71 g, 57%) as white crystals.

Mp 129–130° C.; NMR δ9.66 (s, 1H), 8.00–7.07 (m, 6H), 3.92 (s, 2H), 2.20 (s, 3H).

Preparation 22

5-Amino-1-benzyl-1,2,3-triazole-4-carboxylic acid o-toluamide

A mixture of sodium (0.598 g, 26 mmol) and ethanol (50 mL) was stirred until all the sodium had reacted to form sodium ethoxide. To this solution was added cyanoacetic acid o-toluamide (2.32 g, 13 mmol). The mixture briefly became homogeneous and yellow, then a yellow solid precipitated. At this point benzyl azide (1.73 mL, 13 mmol) was added and the reaction was stirred at ambient temperature for 17 hours. The mixture was concentrated and the yellow solid residue was slurried in water and acidified to pH 4 by addition of acetic acid. The slurry was stirred 30 minutes and the bright red solid which formed was collected and dried (5.2 g). The solid was flash chromatographed on silica gel (100 g) eluting with 0.05% ammonium hydroxide/1% methanol/methylene chloride to afford 3.5 g of impure product in two fractions. This crude product was recrystallized from 16% methanol/isopropyl ether to afford 5-amino-1-benzyl-1,2,3-triazole-4-carboxylic acid o-toluamide (1.52 g, 38%) as a pale orange solid.

Mp 140–144° C.; NMR δ8.54 (s, 1 h), 8.00 (d, J=7.9 Hz, 1H), 7.43–7.22 (m, 7H), 7.07 (t, J 7.5 Hz, 1H), 5.41 (s, 2H), 4.86 (s, 2H), 2.37 (s, 3H). Concentration of the mother liquors afforded an additional 0.618 g of product.

Preparation 23

1-Benzyl-5-methyl-6-o-tolyl-3,6-dihydro-[1,2,3]triazolo[4,5-d]pyrimidin-7-one A mixture of sodium (1.14 g, 49.5 mmol) and ethanol (100 mL) was stirred until all the sodium had reacted to form sodium ethoxide. To this solution was added 5-amino-1-benzyl-1,2,3-triazole-4-carboxylic acid o-toluamide (7.6 g, 24.7 mmol) and ethyl acetate (50 mL). The reaction was refluxed 48 hours, cooled, and concentrated to an orange solid. This solid was partitioned between water and methylene chloride. The phases were separated and the organic layer was dried over magnesium sulfate. Concentration of this organic phase afforded 0.5 g of product. The aqueous layer from the extraction was acidified to pH 6.5 with acetic acid and extracted with chloroform (2×100 mL). Methanol (20 mL) was added to the chloroform to help keep the product from precipitating. This organic phase was dried over magnesium sulfate and concentrated to give 6.93 g of white crystals. The products were combined to yield 7.43 g (90%) of 1-benzyl-5-methyl-6-o-tolyl-3,6-dihydro-[1,2,3]triazolo[4,5-d]pyrimidin-7-one.

Mp 178–180° C.; NMR (DMSO d6) δ9.86 (s, 1H), 7.49–7.09 (m, 6H), 5.49 (s, 2H), 2.24 (s, 3H), 2.05 (br s, 3H).

Preparation 24

5-Methyl-6-o-tolyl-3,6-dihydro-[1,2,3]triazolo[4,5-d]pyrimidin-7-one

A mixture of 1-benzyl-5-methyl-6-o-tolyl-3,6-dihydro-[1,2,3]triazolo[4,5-d]pyrimidin-7-one (4.0 g, 12.07 mmol), acetic acid (150 mL), ethanol (25 mL), and palladium hydroxide on carbon (4.0 g) was hydrogenated on a Parr apparatus. After 5 hours the catalyst was filtered off and replaced with fresh palladium hydroxide on carbon (4.0 g). The hydrogenation was continued 48 hours longer. The reaction was filtered and the filtrate was concentrated to afford 5-methyl-6-o-tolyl-3,6-dihydro-[1,2,3]triazolo[4,5-d]pyrimidin-7-one (0.488 g, 17%) as a white powder.

NMR δ9.31 (s, 1H), 7.85 (m, 1H), 7.30–6.95 (m, 3H), 1.88 (s, 6H). The product was used without purification.

Preparation 25

4-Methylthiazole-2-carboxaldehyde

A solution of 4-methylthiazole (0.91 mL, 10.0 mmol) in tetrahydrofuran (30 mL) was chilled to −78° C. and butyllithium (6.0 mL, 15 mmol, 2.5 molar solution in hexane) was added dropwise over 15 min. The pale yellow solution was stirred 1 h at −78° C. and became thick slurry. Dimethylformamide (1.2 mL, 15 mmol) was added to the reaction via syringe over 5 min. The reaction was stirred an additional 2 h at −79° C., then allowed to warm at 0° C. and poured onto wet ice. The acidity of the mixture was adjusted to pH 4 with 1 N HCl and extracted with ether. The combined ether extracts were washed with brine, dried over sodium sulfate and concentrated afford 4-methylthiazole-2-carboxaldehyde (0.734 g, 57%) as a brown oil.

NMR δ9.88 (s, 1H), 7.29 (s, 1H), 2.50 (s, 3H). The material was used without further purification.

Preparation 26

2-Methylthiazole-4-carboxaldehyde

A solution of ethyl 2-methylthiazole-4-carboxylate (1.0 g, 5.8 mmol) in tetrahydrofuran (35 mL) was chilled to −50° C. and diisobutylaluminum hydride (12 mL, 11.97 mmol, 1 molar solution in tetrahydrofuran) was added dropwise via syringe over 15 min. The solution was stirred 30 min at −50° C., then allowed to warm to ambient temperature over 3 h. The reaciton was chilled over wet ice and carefully quenched with 10 mL of 50% methanol/tetrahydrofuran. The reaction was treated with half saturated aqueous sodium potassium tartrate (Rochelle's salt) and the mixture was filtered. The filter pad was thoroughly washed with ether and water. The entire filtrate was combined and extracted with ethyl acetate. The combined organic layer was washed with brine, dried over sodium sulfate and concentrated to 4-hyrdoxymethyl-2-methylthiazole (0.57 g, 76%) as a tan oil.

NMR δ6.97 (s, 1H), 4.54 (s, 2H), 4.43 (br s, 1H), 2.63 (2, 3H). This material was used without further purification.

An ambient temperature solution of 4-hydroxymethyl-2-methylthiazole (1.0 g, 7.75 mmol) and dichloromethane (50 mL) was treated with Dess-Martin periodinane (4.12 g, 9.69 mmol) all at once. The mixture was allowed to stir overnight. Additional periodinane (1.2 g) was added and the reaction was allowed to stir 4 hours more. The reaction was poured into 50 mL of saturated aqueous sodium thiosulfate and extracted with methylene chloride. The combined organic layer was washed with saturated aqueous sodium bicarbonate and brine, dried over sodium sulfate, and concentrated to afford 0.901 g (92%) of 2-methylthiazole-4-carboxaldehyde as an off white waxy solid which had: NMR 679.96 (s, 1H), 8.03 (s, 1H), 2.77 (s, 3H). The product was suitable for use without purification.

Preparation 27

2-Dimethylaminomethylthiazole-4-carboxaldehyde

To a slurry of 2-dimethylaminothioacetamide hydrochloride (7.7 g, 50 mmol) in ethanol (100 mL) was added ethyl bromopyruvate (6.3 mL). The mixture was refluxed 6 hours and then cooled to room temperature. More ethyl bromopyruvate (3.2 mL for a total of 75 mmol) was added and the reaction was refluxed 2.5 hours more. The mixture was cooled to ambient temperature and concentrated at reduced pressure. The residue was partitioned between water and ethyl acetate and brought to pH 10 with addition of solid potassium carbonate. The phases were separated and the aqueous layer was extracted with ethyl acetate. The combined organic phase was washed with water and brine, then it was dried over sodium sulfate and concentrated to afford an amber oil. This oil was purified by flash chromatography on silica gel (120 g). Elution proceeded as follows: 2% methanol/chloroform 200 mL, forerun; 10% methanol/chloroform, 75 mL, nil; 750 mL, 10.7 g (100%) of ethyl 2-dimethylaminomethylthiazole-4-carboxylate as a clear yellow oil. The material was suitable for use without further purification.

NMR δ8.07 (d, J=1.4 Hz, 1H), 4.32 (q, J=7 Hz, 2H), 3.73 (s, 2H), 2.28 (s, 6H), 1.31 (t, J=7 Hz, 3H).

To a mixture of lithium aluminum hydride (4.5 g, 119 mmol) in ice cold tetrahydrofuran (100 mL) was added ethyl 2-dimethylaminomethylthiazole-4-carboxylate (8.5 g, 39.7 mmol in 40 mL of tetrahydrofuran) dropwise over 40 min maintaining an internal temperature of 5–10° C. The mixture was stirred at this temperature range for 90 min. The reaction was carefully quenched with saturated aqueous ammonium chloride (30 mL). The resulting gray slurry was stirred 15 min and filtered through celite. The pad was well washed with ethyl acetate. The filtrate was washed with brine and dried over sodium sulfate. Concentration of this organic solution gave 4.2 g (62%) of 2-dimethylaminomethyl-4-hydroxymethylthiazole as an amber oil. The material was used without further purification.

NMR δ7.12 (s, 1H), 4.71 (s, 2H), 3.73 (s, 2H), 2.50 (br s, 1H), 2.32 (s, 6H).

A solution of 2-dimethylaminomethyl-4-hydroxymethylthiazole (4.2 g, 27.3 mmol) in methylene chloride (200 mL) was treated with Dess-Martin reagent (14.5 g, 34.1 mmol). The mixture was stirred at ambient temperature for 24 hours. Additional Dess-Martin reagent (2.9 g) was added and the mixture was stirred 4 hours more. The reaction was quenched by addition of saturated aqueous sodium thiosulfate (100 mL) and the pH of the resulting mixture was adjusted to a pH of 10 by addition of solid potassium carbonate. The two phase mixture was filtered. The phases were separated from the filtrate and the aqueous layer was extracted with methylene chloride. The combined organic layers were washed with brine, dried over sodium sulfate, and concentrated to afford a yellow solid. This solid was purified by flash chromatography on silica gel (50×130 mm) eluting first with chloroform (200 mL) and then 2% methanol/chloroform collecting 25 mL fractions. Fractions 51–80 were combined and concentrated to leave 2.9 g of a milky yellow oil. This oil was triturated with 50% ethereal chloroform and a solid was removed by filtration. The filtrate was concentrated to yield 2.6 g (62%) of 2-dimethylaminomethyl-thiazole-4-carboxaldehyde as a yellow oil. This product was used without further purification.

NMR δ9.95 (s, 1H), 8.14 (s, 1H), 3.81 (s, 2H), 2.36 (s, 6H).

We claim:

1. A bicyclic compound of the formula

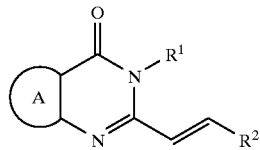

wherein ring A is a fused 5 membered heteroaromatic ring which, taken together with the carbon atoms common to both rings of the bicyclic system, has the formula

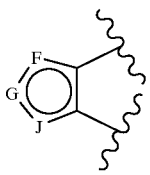

wherein one of said ring positions "F", "G" and "J" is selected from nitrogen, oxygen or sulfur, and the other two of said ring positions "F", "G", and "J" are carbons;

wherein said fused heteroaromatic rings may optionally be independently substituted on any of the carbon or nitrogen atoms capable of forming an additional bond with a substituent selected from hydrogen, $(C_1-C_6)$ alkyl, halogen, trifluoromethyl, amino-$(CH_2)_n$—, $(C_1-C_6)$alkylamino-$CH_2)_n$—, di$(C_1-C_6)$alkyl-amino-$(CH_2)_n$—, $(C_1-C_6)$alkoxy, hydroxy $(C_1-C_6)$alkyl, $(C_1-C_6)$alkyl-O—$(C_1-C_6)$alkyl-, —CN, $(C_1-C_6)$alkyl-CO—O—$(C_1-C_6)$alkyl-, $(C_1-C_6)$alkyl-O—CO—O—$(C_1-C_6)$alkyl, $(C_1-C_6)$alkyl-CO—O—, hydroxy, —$NO_2$, $R^3$—C(=O)—, $R^4$—O—C(=O)—, di$(C_1-C_6)$alkyl-N—C(=O)—, $(C_1-C_6)$cycloalkyl, and $R^4$—NH—C(=O)—, and phenyl optionally substituted with halo, $(C_1-C_6)$ alkyl, —CN, or —$CF_3$;

$R^1$ is substituted phenyl of the formula $Ph^1$ or heteroaryl wherein said heteroaryl is selected from the group consisting of pyridin-2-yl, pyridin-3-yl, pyridin-4-yl, wherein said heteroaryl may optionally be substituted on any of the atoms capable of forming an additional bond, up to a maximum of three substituents, with a substituent selected from hydrogen, $(C_1-C_6)$alkyl, halogen, trifluoromethyl, amino-$(CH_2)_n$—, $(C_1-C_6)$ alkylamino-$(CH_2)_n$—, di$(C_1-C_6)$alkyl-amino-$(CH_2)_n$—, $(C_1-C_6)$alkoxy, hydroxy$(C_1-C_6)$alkyl, $(C_1-C_6)$alkyl-O—$(C_1-C_6)$alkyl-, —CN, $(C_1-C_6)$alkyl-CO—O—$(C_1-C_6)$alkyl-, $(C_1-C_6)$alkyl-O—CO—O—$(C_1-C_6)$alkyl, $(C_1-C_6)$alkyl-CO—O—, hydroxy, H—C(=O)—, $(C_1-C_6)$alkyl-C(=O)—, HO—C(=O)—, $(C_1-C_6)$alkyl-O—C(=O)—, $NH_2$—C(=O)—, $(C_1-C_6)$alkyl-NH—C(=O), and di$(C_1-C_6)$alkyl-NH—C(=O)—;

wherein said $Ph^1$ is a group of the formula

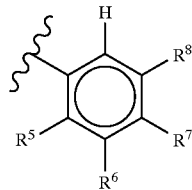

$R^2$ is phenyl of the formula $ph^2$ or a five or six membered heterocycle, wherein said six membered heterocycle has the formula

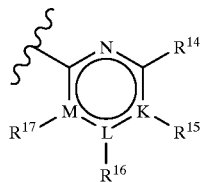

wherein "N" is nitrogen; wherein said ring positions "K", "L" and "M" may be independently selected from carbon or nitrogen, with the proviso that only one of "K", "L" or "M" can be nitrogen;

wherein said five membered heterocycle has the formula

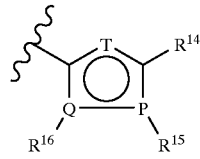

wherein said ring positions "P," "Q" and "T" may be independently selected from carbon, nitrogen, oxygen or sulfur; with the proviso that only one of "P," "Q" or "T" can be oxygen or sulfur and at least one of "P," "Q"0 or "T" must be a heteroatom;

wherein said $Ph^2$ is a group of the formula

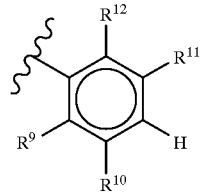

with the proviso that when "G" is sulfur, $R^2$ is not the six membered heterocycle;

$R^3$ is hydrogen or $(C_1-C_6)$ alkyl;

$R^4$ is hydrogen or $(C_1-C_6)$ alkyl;

$R^5$ is hydrogen, $(C_1-C_6)$alkyl, halo, $CF_3$, $(C_1-C_6)$alkoxy or $(C_1-C_6)$ alkylthiol;

$R^6$ is hydrogen or halo;

$R^7$ is hydrogen or halo;

$R^8$ is hydrogen or halo;

$R^9$ is hydrogen, $(C_1-C_6)$alkyl optionally substituted with one to three halogen atoms, halo, $CF_3$, $(C_1-C_6)$alkoxy optionally substituted with one to three halogen atoms, $(C_1-C_6)$alkylthiol, $R^{13}$O—$(CH_2)_p$—, $(C_1-C_6)$alkyl-NH—$(CH_2)_p$—, di$(C_1-C_6)$alkyl-N—$(CH_2)_p$—, $(C_1-C_5)$cycloalkyl-NH—$(CH_2)_p$—, $H_2$N—(C=O)—$(CH_2)_p$—, $(C_1-C_6)$alkyl-HN—(C=O)—$(CH_2)_p$—, di$(C_1-C_6)$alkyl-N—(C=O)—$(CH_2)_p$—, $(C_1-C_5)$cycloalkyl-NH—(C=O)—$(CH_2)_p$—, $R^{13}$O—(C=O)—$(CH_2)_p$—, $(C_1-C_6)$alkyl-(O=C)—O—$(C_1-C_6)$alkyl-, $(C_1-C_6)$alkyl-O—(O=C)—O—$(C_1-C_6)$-alkyl-,

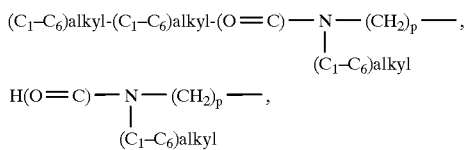

hydroxy, H—C(=O)—(CH$_2$)$_p$—, (C$_1$–C$_6$)alkyl-C(=O)—, (C$_1$–C$_6$)alkyl-O—C(=O)—, R$^4$—(CH$_2$)$_p$—O—C(=O)—, amino-(CH$_2$)$_p$—, hydroxy-(C$_1$–C$_6$)alkyl-, (C$_1$–C$_6$)alkyl-O—(C$_1$–C$_6$)alkyl-, and —CN;

R$^{10}$ and R$^{14}$ are hydrogen, (C$_1$–C$_6$)alkyl optionally substituted with one to three halogen atoms, halo, CF$_3$, (C$_1$–C$_6$)alkoxy optionally substituted with one to three halogen atoms, (C$_1$–C$_6$)alkylthiol, R$^{13}$O—(CH$_2$)$_p$—, (C$_1$–C$_6$)alkyl-NH—(CH$_2$)$_p$—, di(C$_1$–C$_6$)alkyl-N—(CH$_2$)$_p$—, (C$_1$–C$_5$)cycloalkyl-NH—(CH$_2$)$_p$—, H$_2$N—(C=O)—(CH$_2$)$_p$—, (C$_1$–C$_6$)alkyl-HN—(C=O)—(CH$_2$)$_p$—, di(C$_1$–C$_6$)alkyl-N—(C=O)—(CH$_2$)$_p$—, (C$_1$–C$_5$)cycloalkyl-NH—(C=O)—(CH$_2$)$_p$—, R$^{13}$O—(C=O)—(CH$_2$)$_p$—, (C$_1$–C$_6$)alkyl-(O=C)—O—(C$_1$–C$_6$)alkyl-, (C$_1$–C$_6$)alkyl-O—(O=C)—O—(C$_1$–C$_6$)-alkyl, (C$_1$–C$_6$)alkyl-(O=C)—O—, (C$_1$–C$_6$)alkyl-(O=C)—NH—(CH$_2$)$_p$—, H(O=C)—NH—(CH$_2$)$_p$—

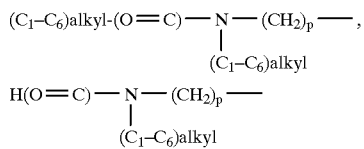

hydroxy, H—C(=O)—(CH$_2$)$_p$—, (C$_1$–C$_6$)alkyl-C(=O)—, (C$_1$–C$_6$)alkyl-O—C(=O)—, R$^4$—(CH$_2$)$_p$—O—C(=O)—, amino-(CH$_2$)$_p$—, hydroxy-(C$_1$–C$_6$)alkyl, (C$_1$–C$_6$)alkyl-O—(C$_1$–C$_6$)alkyl, —CHO and —CN;

R$^{11}$ is hydrogen or halo;

R$^{12}$ is hydrogen or halo;

R$^{13}$ is hydrogen, (C$_1$–C$_6$)alkyl, (C$_1$–C$_6$)alkyl-(C=O)—, (C$_1$–C$_6$)alkyl-O—(C=O)—, (C$_1$–C$_6$)alkyl-NH—(C=O)—, or di(C$_1$–C$_6$)alkyl-N—(C=O)—;

R$^{15}$ is hydrogen, —CN, (C$_1$–C$_6$)alkyl, halo, CF$_3$, —CHO or (C$_1$–C$_6$)alkoxy;

R$^{16}$ is hydrogen, —CN, (C$_1$–C$_6$)alkyl, halo, CF$_3$, —CHO or (C$_1$–C$_6$)alkoxy;

R$^{17}$ is hydrogen, —CN, (C$_1$–C$_6$)alkyl, halo, CF$_3$, CHO or (C$_1$–C$_6$)alkoxy;

n is an integer from zero to 3;

p is an integer from zero to 3;

with the proviso that when R$^9$ is hydrogen, then one of R$^{11}$ and R$^{12}$ is other than hydrogen;

and the pharmaceutically acceptable salts of such compounds.

2. A compound according to claim 1 wherein the "G" or "F" heteroatoms of the 5-memebered heteroaromatic ring are sulfur.

3. A compound according to claim 1 wherein the A ring is a 5-membered heteroaromatic ring and "G" is sulfur and "F" and "J" are carbon.

4. A compound according to claim 1 wherein the A ring is a 5-membered heteroaromatic ring and F" is sulfur and "G" and "J" are carbon.

5. A compound according to claim 1 wherein R$^1$ is Ph$^1$ and one of R$^5$, R$^6$, R$^7$ or R$^8$ is fluoro, bromo, chloro, methyl or trifluoromethyl.

6. A compound according to claim 1 wherein R$^1$ is Ph$^1$ or pyridin-3-yl and R$^5$ is fluoro, bromo, chloro, methyl or trifluoromethyl.

7. A compound according to claim 2 wherein R$^1$ is Ph$^1$ and R$^5$ is fluoro, bromo, chloro, methyl or trifluoromethyl.

8. A compound according to claim 3 wherein R$^1$ is Ph$^1$ and R$^5$ is fluoro, bromo, chloro, methyl or trifluoromethyl.

9. A compound according to claim 4 wherein R$^1$ is Ph$^1$ and R$^5$ is fluoro, bromo, chloro, methyl or trifluoromethyl.

10. A compound according to claim 1 wherein R$^2$ is Ph$^2$ and R$^9$ is fluoro, chloro, hydroxy or cyano.

11. A compound according to claim 2 wherein R$^2$ is Ph$^2$ and R$^9$ is fluoro, chloro, hydroxy or cyano.

12. A compound according to claim 3 wherein R$^2$ is Ph$^2$ and R$^9$ is fluoro, chloro, hydroxy or cyano.

13. A compound according to claim 4 wherein R$^2$ is Ph$^2$ and R$^9$ is fluoro, chloro, hydroxy or cyano.

14. A compound according to claim 6 wherein R$^2$ is Ph$^2$ and R$^9$ is fluoro, chloro, hydroxy or cyano.

15. A compound according to claim 7 wherein R$^2$ is Ph$^2$ and R$^9$ is fluoro, chloro, hydroxy or cyano.

16. A compound according to claim 9 wherein R$^2$ is Ph$^2$ and R$^9$ is fluoro, chloro, hydroxy or cyano.

17. A compound according to claim 1 wherein R$^1$ is pyridin-3-yl optionally substituted with halo, —CN, CF$_3$, or (C$_1$–C$_6$)alkyl.

18. A compound according to claim 2 wherein R$^1$ is pyridin-3-yl optionally substituted with halo, —CN, CF$_3$, or (C$_1$–C$_6$)alkyl.

19. A compound according to claim 3 wherein R$^1$ is pyridin-3-yl optionally substituted with halo, —CN, CF$_3$, or (C$_1$–C$_6$)alkyl.

20. A compound according to claim 4 wherein R$^1$ is pyridin-3-yl optionally substituted with halo, —CN, CF$_3$, or (C$_1$–C$_6$)alkyl.

21. A compound according to claim 14 wherein R$^1$ is pyridin-3-yl optionally substituted with halo, —CN, CF$_3$, or (C$_1$–C$_6$)alkyl.

22. A compound according to claim 1 wherein R$^2$ is optionally substituted pyrid-2-yl, 1,3-thiazol-4-yl, 1,3-thiazol-2-yl or fur-2-yl.

23. A compound according to claim 2 wherein R$^2$ is optionally substituted pyrid-2-yl, 1,3-thiazol-4-yl, 1,3-thiazol-2-yl or fur-2-yl.

24. A compound according to claim 3 wherein R$^2$ is optionally substituted 1,3-thiazol-4-yl, 1,3-thiazol-2-yl or fur-2-yl.

25. A compound according to claim 4 wherein R$^2$ is optionally substituted pyrid-2-yl, 1,3-thiazol-4-yl, 1,3-thiazol-2-yl or fur-2-yl.

26. A compound according to claim 9 wherein R$^2$ is optionally substituted pyrid-2-yl, 1,3-thiazol-4-yl, 1,3-thiazol-2-yl or fur-2-yl.

27. A compound according to claim 17 wherein R$^2$ is optionally substituted pyrid-2-yl, 1,3-thiazol-4-yl, 1,3-thiazol-2-yl or fur-2-yl.

28. A compound according to claim 1 wherein said compound is:

3-(2-methylphenyl)-2-[2-(2-fluoro-phenyl)-vinyl]-3H-thieno[3,2-d]pyrimidin-4-one;

3-(2-chlorophenyl)-2-[2-(2-fluoro-phenyl)-vinyl]-3H-thieno[3,2-d]pyrimidin-4-one;

3-(2-methylphenyl)-2-[2-pyrid-2-yl-vinyl]-3H-thieno[3,2-d]pyrimidin-4-one;

3-(2-methylphenyl)-2-[2-chlorophenyl-vinyl]-3H-thieno[3,2-d]pyrimidin-4-one;

3-(2-trifluoromethyl-phenyl)-2-[2-fluorophenyl-vinyl]-3H-thieno[3,2-d]pyrimidin-4-one;

3-(2-chloro-pyridin-3-yl)-2-[2-(2-methyl-thiazol-4-yl)-vinyl]-3H-thieno[3,2-]pyrimidin-4-one;

3-(2-methyl-pyridin-3-yl)-2-[2-(2-methyl-thiazol-4-yl)-vinyl]-3H-thieno[3,2d]pyrimidin-4-one;

3-(2-chlorophenyl)-2-[2-pyrid-2-yl-vinyl]-3H-thieno[3,2-d]pyrimidin-4-one; or 3-(2-chlorophenyl)-2-[2-hydroxyphenyl-vinyl]-3H-thieno[3,2-d]pyrimidin-4-one.

29. A compound according to claim 1, wherein said compound is 3-(2-methylphenyl)2-[2-(2-fluorophenyl)-vinyl]-3H-thieno[3,2-d]pyrimidin-4-one.

30. A compound according to claim 1, wherein said compound is 3-(2-methylphenyl)2-[2-(2-methyl-1,3-thiazol-4-yl)-vinyl]-3H-thieno[3,2-d]pyrimidin-4-one.

31. A compound according to claim 1, wherein said compound is 3-(2-chloropyrid-3-yl)2-[2-(2-methylthiazol-4-yl)-vinyl]-3H-thieno[3,2-d]pyrimidin-4-one.

32. A compound according to claim 1, wherein said compound is 3-(2-methylphenyl)2-[2-(4-methyl-(1,3)-thiazol-2-yl)-vinyl]-3H-thieno[3,2-d]pyrimidin-4-one.

33. A pharmaceutical composition for treating a condition selected from cerebral deficits subsequent to cardiac bypass surgery and grafting, stroke, cerebral ischemia, spinal cord trauma, head trauma, Alzheimer's disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia, arrest, hypoglycemic neuronal damage, opiate tolerance, addiction withdrawal, ocular damage, retinopathy, retinal neuropathy, tinnitus, idiopathic and drug induced Parkinson's Disease, anxiety, emesis, brain edema, chronic or acute pain, or tardive dyskinesia, in a mammal, comprising an amount of a compound according to claim 1 effective in treating such condition and a pharmaceutically acceptable carrier.

34. A pharmaceutical composition for treating disorders the treatment of which is facilitated by enhanced glutamate neurotransmission in a mammal, comprising an amount of a compound according to claim 1 effective in treating such condition and a pharmaceutically acceptable carrier.

35. A pharmaceutical composition for treating a condition selected from cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia, cardiac arrest, hypoglycemic neuronal damage, opiate tolerance, addiction withdrawal, ocular damage, retinopathy, retinal neuropathy, tinnitus, idiopathic and drug induced Parkinson's disease, anxiety, emesis, brain edema, chronic or acute pain, or tardive dyskinesia, in a mammal, comprising an AMPA receptor antagonizing effective amount of a compound according to claim 1 and a pharmaceutically acceptable carrier.

36. A pharmaceutical composition for treating disorders the treatment of which is facilitated by enhanced glutamate neurotransmission in a mammal, comprising an AMPA receptor antagonizing effective amount of a compound according to claim 1 and a pharmaceutically acceptable carrier.

37. A method for treating a condition selected from cerebral deficits subsequent to cardiac bypass surgery and grafting, stroke, cerebral ischemia, spinal cord trauma, head trauma, Alzheimer's Disease, AIDS-induced dementia, migraine headaches, urinary incontinence, psychosis, perinatal hypoxia, hypoxia arrest, hypoglycemic neuronal damage, opiate tolerance, addiction withdrawal, ocular damage, retinopathy, retinal neuropathy, tinnitus, anxiety, emesis, brain edema, or chronic or acute pain in a mammal comprising administering to a mammal in need of such treatment an amount effective in treating such condition of a bicyclic compound or pharmaceutically acceptable salt of said bicyclic compound of the formula

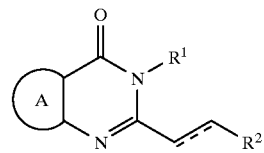

wherein ring A is a fused 5 membered heteroaromatic ring which, taken together with the carbon atoms common to both rings of the bicyclic system, has the formula

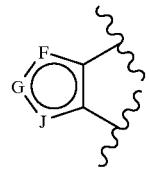

wherein one of said ring positions "F", "G" and "J" is selected from nitrogen, oxygen or sulfur, and the other two of said ring positions "F", "G", and "J" are carbons;

wherein said fused heteroaromatic rings may optionally be independently substituted on any of the carbon or nitrogen atoms capable or forming an additional bond with a substituent selected from hydrogen, $(C_1-C_6)$ alkyl, halogen, trifluoromethyl, amino-$(CH_2)_n$—, $(C_1-C_6)$alkylamino-$(CH_2)_n$—, di$(C_1-C_6)$alkyl-amino-$(CH_2)_n$—, $(C_1-C_6)$alkoxy, hydroxy $(C_1-C_6)$alkyl, $(C_1-C_6)$alkyl-O—$(C_1-C_6)$alkyl-, —CN, $(C_1-C_6)$alkyl-CO—O—$(C_1-C_6)$alkyl-, $(C_1-C_6)$alkyl-O—CO—O—$(C_1-C_6)$alkyl, $(C_1-C_6)$alkyl-CO—O—, hydroxy, —$NO_2$, $R^3$—C(=O)—, $R^4$—O—C(=O)—, di$(C_1-C_6)$alkyl-N—C(=O)—, $(C_1-C_6)$cycloalkyl, and $R^4$—NH—C(=O)—, and phenyl optionally substituted with halo, $(C_1-C_6)$ alkyl, —CN, or —$CF_3$;

$R^1$ is substituted phenyl of the formula $Ph^1$ or heteroaryl wherein said heteroaryl is selected from the group consisting of pyridin-2-yl, pyridin-3-yl, pyridin-4-yl, wherein said heteroaryl may optionally be substituted on any of the atoms capable of forming an additional bond, up to a maximum of three substituents, with a substituent selected from hydrogen, $(C_1-C_6)$alkyl, halogen, trifluoromethyl, amino-$(CH_2)_n$—, $(C_1-C_6)$alkylamino-$(CH_2)_n$—, di$(C_1-C_6)$alkyl-amino-$(CH_2)_n$—, $(C_1-C_6)$alkoxy, hydroxy$(C_1-C_6)$alkyl, $(C_1-C_6)$alkyl-O—$(C_1-C_6)$alkyl-, —CN, $(C_1-C_6)$alkyl-CO—O—$(C_1-C_6)$alkyl-, $(C_1-C_6)$alkyl-O—CO—O—$(C_1-C_6)$alkyl, $(C_1-C_6)$alkyl-CO—O—, hydroxy, H—C(=O)—, $(C_1-C_6)$alkyl-C(=O)—, HO—C(=O)—, $(C_1-C_6)$alkyl-O—C(=O)—, $NH_2$—C(=O)—, $(C_1-C_6)$alkyl-NH—C(=O), and di$(C_1-C_6)$alkyl-NH—C(=O)—;

wherein said Ph$^1$ is a group of the formula

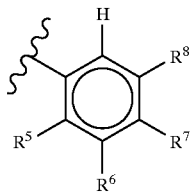

R$^2$ is phenyl of the formula Ph$^2$ or a five or six membered heterocycle, wherein said six membered heterocycle has the formula

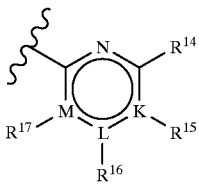

wherein "N" is nitrogen; wherein said ring positions "K", "L" and "M" may be independently selected from carbon or nitrogen, with the proviso that only one of "K", "L" or "M" can be nitrogen;

wherein said five membered heterocycle has the formula

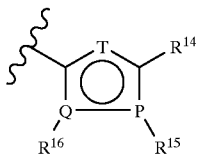

wherein said ring positions "P," "Q" and "T" may be independently selected from carbon, nitrogen, oxygen or sulfur; with the proviso that only one of "P," "Q" or "T" can be oxygen or sulfur and at least one of "P," "Q" or "T" must be a heteroatom;

wherein said Ph$^2$ is a group of the formula

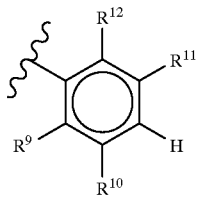

R$^3$ is hydrogen or (C$_1$–C$_6$) alkyl;
R$^4$ is hydrogen or (C$_1$–C$_6$) alkyl;
R$^5$ is hydrogen, (C$_1$–C$_6$)alkyl, halo, CF$_3$, (C$_1$–C$_6$)alkoxy or (C$_1$–C$_6$)alkylthiol;
R$^6$ is hydrogen or halo;
R$^7$ is hydrogen or halo;
R$^8$ is hydrogen or halo;
R$^9$ is hydrogen, (C$_1$–C$_6$)alkyl optionally substituted with one to three halogen atoms, halo, CF$_3$, (C$_1$–C$_6$)alkoxy optionally substituted with one to three halogen atoms, (C$_1$–C$_6$)alkylthiol, R$^{13}$O—(CH$_2$)$_p$—, (C$_1$–C$_6$)alkyl-NH—(CH$_2$)$_p$—, di(C$_1$–C$_6$)alkyl-N—(CH$_2$)$_p$—, (C$_1$–C$_5$)cycloalkyl-NH—(CH$_2$)$_p$—, H$_2$N—(C=O)—(CH$_2$)$_p$—, (C$_1$–C$_6$)alkyl-HN—(C=O)—(CH$_2$)$_p$—, di(C$_1$–C$_6$)alkyl-N—(C=O)—(CH$_2$)$_p$—, (C$_1$–C$_5$)cycloalkyl-NH—(C=O)—(CH$_2$)$_p$—, R$^{13}$O—(C=O)—(CH$_2$)$_p$—, (C$_1$–C$_6$)alkyl-(O=C)—O—(C$_1$–C$_6$)alkyl-, (C$_1$–C$_6$)alkyl-O—(O=C)—O—(C$_1$–C$_6$)-alkyl-, (C$_1$—C$_6$)alkyl-(C$_1$—C$_6$)alkyl-(O=C)—N—(CH$_2$)$_p$—,
　　　　　　　　　　　　　　　　　　　　　|
　　　　　　　　　　　　　　　　　　　(C$_1$—C$_6$)alkyl H(O=C)—N—(CH$_2$)$_p$—,
　　　　　|
　　(C$_1$—C$_6$)alkyl hydroxy, H—C(=O)—(CH$_2$)$_p$—, (C$_1$–C$_6$)alkyl-C(=O)—, (C$_1$–C$_6$)alkyl-O—C(=O)—, R$^4$—(CH$_2$)$_p$—O—C(=O)—, amino-(CH$_2$)$_p$—, hydroxy-(C$_1$–C$_6$)alkyl-, (C$_1$–C$_6$)alkyl-O—(C$_1$–C$_6$)alkyl-, and —CN;

R$^{10}$ and R$^{14}$ are hydrogen, (C$_1$–C$_6$)alkyl optionally substituted with one to three halogen atoms, halo, CF$_3$, (C$_1$–C$_6$)alkoxy optionally substituted with one to three halogen atoms, (C$_1$–C$_6$)alkylthiol, R$^{13}$O—(CH$_2$)$_p$—, (C$_1$–C$_6$)alkyl-NH—(CH$_2$)$_p$—, di(C$_1$–C$_6$)alkyl-N—(CH$_2$)$_p$—, (C$_1$–C$_5$)cycloalkyl-NH—(CH$_2$)$_p$—, H$_2$N—(C=O)—(CH$_2$)$_p$—, (C$_1$–C$_6$)alkyl-HN—(C=O)—(CH$_2$)$_p$—, di(C$_1$–C$_6$)alkyl-N—(C=O)—(CH$_2$)$_p$—, (C$_1$–C$_5$)cycloalkyl-NH—(C=O)—(CH$_2$)$_p$—, R$^{13}$O—(C=O)—(CH$_2$)$_p$—, (C$_1$–C$_6$)alkyl-(O=C)—O—(C$_1$–C$_6$)alkyl-, (C$_1$–C$_6$)alkyl-O—(O=C)—O—(C$_1$–C$_6$)—alkyl-, (C$_1$–C$_6$)alkyl-(O=C)—O—, (C$_1$–C$_6$)alkyl-(O=C)—NH—(CH$_2$)$_p$—, H(O=C)—NH—(CH$_2$)$_p$—, (C$_1$—C$_6$)alkyl-(O=C)—N—(CH$_2$)$_p$—,
　　　　　　　　　　　　　　　|
　　　　　　　　　　　　(C$_1$—C$_6$)alkyl H(O=C)—N—(CH$_2$)$_p$—
　　　　　|
　　(C$_1$—C$_6$)alkyl hydroxy, H—C(=O)—(CH$_2$)$_p$—, (C$_1$–C$_6$)alkyl-C(=O)—, (C$_1$–C$_6$)alkyl-O—C(=O)—, R$^4$—(CH$_2$)$_p$—O—C(=O)—, amino-(CH$_2$)$_p$—, hydroxy-(C$_1$–C$_6$)alkyl, (C$_1$–C$_6$)alkyl-O—(C$_1$–C$_6$)alkyl, —CHO and —CN;

R$^{11}$ is hydrogen or halo;
R$^{12}$ is hydrogen or halo;
R$^{13}$ is hydrogen, (C$_1$–C$_6$)alkyl, (C$_1$–C$_6$)alkyl-(C=O)—, (C$_1$–C$_6$)alkyl-O—(C=O)—, (C$_1$–C$_6$)alkyl-NH—(C=O)—, or di(C$_1$–C$_6$)alkyl-N—(C=O)—;
R$^{15}$ is hydrogen, —CN, (C$_1$–C$_6$)alkyl, halo, CF$_3$, —CHO or (C$_1$–C$_6$)alkoxy;
R$^{16}$ is hydrogen, —CN, (C$_1$–C$_6$)alkyl, halo, CF$_3$, —CHO or (C$_1$–C$_6$)alkoxy;
R$^{17}$ is hydrogen, —CN, (C$_1$–C$_6$)alkyl, halo, CF$_3$, CHO or (C$_1$–C$_6$)alkoxy;
n is an integer from zero to 3;
p is an integer from zero to 3;
wherein the dashed bond represents an optional double bond;
with the proviso that when R$^9$ is hydrogen, then one of R$^{11}$ and R$^{12}$ is other than hydrogen.

38. A method for treating disorders the treatment of which is facilitated by enhanced glutamate nourotransmission in a mammal, comprising administering to a mammal requiring such treatment an amount effective in treating such condition of a bicyclic compound, or pharmaceutically acceptable salt of said bicyclic compound, of the formula

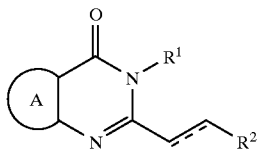

wherein ring A is a fused 5 membered heteroaromatic ring which, taken together with the carbon atoms common to both rings of the bicyclic system, has the formula

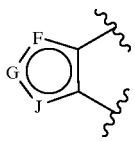

wherein one of said ring positions "F", "G" and "J" is selected from nitrogen, oxygen or sulfur, and the other two of said ring positions "F", "G", and "J" are carbons;

wherein said fused heteroaromatic rings may optionally be independently substituted on any of the carbon or nitrogen atoms capable of forming an additional bond with a substituent selected from hydrogen, $(C_1-C_6)$ alkyl, halogen, trifluoromethyl, amino-$(CH_2)_n$—, $(C_1-C_6)$alkylamino-$(CH_2)_n$—, di$(C_1-C_6)$alkyl-amino-$(CH_2)_n$—, $(C_1-C_6)$alkoxy, hydroxy$(C_1-C_6)$alkyl, $(C_1-C_6)$alkyl-O—$(C_1-C_6)$alkyl-, —CN, $(C_1-C_6)$alkyl-CO—O—$(C_1-C_6)$alkyl-, $(C_1-C_6)$alkyl-O—CO—O—$(C_1-C_6)$alkyl, $(C_1-C_6)$alkyl-CO—O—, hydroxy, —$NO_2$, $R^3$—C(=O)—, $R^4$—O—C(=O)—, di$(C_1-C_6)$alkyl-N—C(=O)—, $(C_1-C_6)$cycloalkyl, and $R^4$—NH—C(=O)—, and phenyl optionally substituted with halo, $(C_1-C_6)$ alkyl, —CN, or —$CF_3$;

$R^1$ is substituted phenyl of the formula $Ph^1$ or heteroaryl wherein said heteroaryl is selected from the group consisting of pyridin-2-yl, pyridin-3-yl, pyridin-4-yl, wherein said heteroaryl may optionally be substituted on any of the atoms capable of forming an additional bond, up to a maximum of three substituents, with a substituent selected from hydrogen, $(C_1-C_6)$alkyl, halogen, trifluoromethyl, amino-$(CH_2)_n$—, $(C_1-C_6)$alkylamino-$(CH_2)_n$—, di$(C_1-C_6)$alkyl-amino-$(CH_2)_n$—, $(C_1-C_6)$alkoxy, hydroxy$(C_1-C_6)$alkyl, $(C_1-C_6)$alkyl-O—$(C_1-C_6)$alkyl-, —CN, $(C_1-C_6)$alkyl-CO—O—$(C_1-C_6)$alkyl-, $(C_1-C_6)$alkyl-O—CO—O—$(C_1-C_6)$alkyl, $(C_1-C_6)$alkyl-CO—O—, hydroxy, H—C(=O)—, $(C_1-C_6)$alkyl-C(=O)—, HO—C(=O)—, $(C_1-C_6)$alkyl-O—C(=O)—, $NH_2$—C(=O)—, $(C_1-C_6)$alkyl-NH—C(=O), and di$(C_1-C_6)$alkyl-NH—C(=O)—;

wherein said $Ph^1$ is a group of the formula

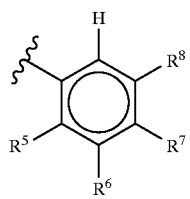

$R^2$ is phenyl of the formula $Ph^2$ or a five or six membered heterocycle, wherein said six membered heterocycle has the formula

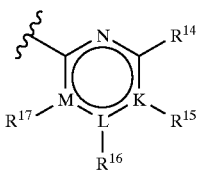

wherein "N" is nitrogen; wherein said ring positions "K", "L" and "M" may be independently selected from carbon or nitrogen, with the proviso that only one of "K", "L" or "M" can be nitrogen;

wherein said five membered heterocycle has the formula

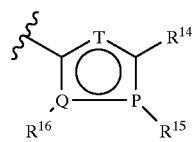

wherein said ring positions "P," "Q" and "T" may be independently selected from carbon, nitrogen, oxygen or sulfur; with the proviso that only one of "P," "Q" or "T" can be oxygen or sulfur and at least one of "P," "Q" or "T" must be a heteroatom;

wherein said $Ph^2$ is a group of the formula

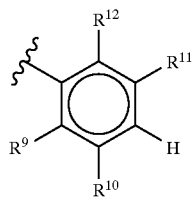

$R^3$ is hydrogen or $(C_1-C_6)$ alkyl;
$R^4$ is hydrogen or $(C_1-C_6)$ alkyl;
$R^5$ is hydrogen, $(C_1-C_6)$alkyl, halo, $CF_3$, $(C_1-C_6)$alkoxy or $(C_1-C_6)$alkylthiol;
$R^6$ is hydrogen or halo;
$R^7$ is hydrogen or halo;
$R^8$ is hydrogen or halo;
$R^9$ is hydrogen, $(C_1-C_6)$alkyl optionally substituted with one to three halogen atoms, halo, $CF_3$, $(C_1-C_6)$alkoxy optionally substituted with one to three halogen atoms, $(C_1-C_6)$alkylthiol, $R^{13}$O—$(CH_2)_p$—, $(C_1-C_6)$alkyl-NH—$(CH_2)_p$—, di$(C_1-C_6)$alkyl-N—$(CH_2)_p$—, $(C_1-C_5)$cycloalkyl-NH—$(CH_2)_p$—, $H_2N$—(C=O)—

$(CH_2)_p$—, $(C_1-C_6)$alkyl-HN—(C=O)—$(CH_2)_p$—, di$(C_1-C_6)$alkyl-N—(C=O)—$(CH_2)_p$—, $(C_1-C_5)$cycloalkyl-NH—(C=O)—$(CH_2)_p$—, $R^{13}$O—(C=O)—$(CH_2)_p$—, $(C_1-C_6)$alkyl-(O=C)—O—$(C_1-C_6)$alkyl-, $(C_1-C_6)$alkyl-O—(O=C)—O—$(C_1-C_6)$-alkyl-,

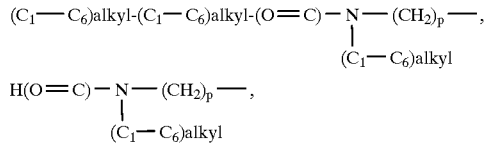

hydroxy, H—C(=O)—$(CH_2)_p$—, $(C_1-C_6)$alkyl-C(=O)—, $(C_1-C_6)$alkyl-O—C(=O)—, $R^4$—$(C_2)_p$—O—C(=O)—, amino-$(CH_2)_p$—, hydroxy-$(C_1-C_6)$alkyl-, $(C_1-C_6)$alkyl-O—$(C_1-C_6)$alkyl-, and —CN;

$R^{10}$ and $R^{14}$ are hydrogen, $(C_1-C_6)$alkyl optionally substituted with one to three halogen atoms, halo, $CF_3$, $(C_1-C_6)$alkoxy optionally substituted with one to three halogen atoms, $(C_1-C_6)$alkylthiol, $R^{13}$O—$(CH_2)_p$—, $(C_1-C_6)$alkyl-NH—$(CH_2)_p$—, di$(C_1-C_6)$alkyl-N—$(CH_2)_p$—, $(C_1-C_5)$cycloalkyl-NH—$(CH_2)_p$—, $H_2$N—(C=O)—$(CH_2)_p$—, $(C_1-C_6)$alkyl-HN—(C=O)—$(CH_2)_p$—, di$(C_1-C_6)$alkyl-N—(C=O)—$(CH_2)_p$—, $(C_1-C_5)$cycloalkyl-NH—(C=O)—$(CH_2)_p$—, $R^{13}$O—(C=O)—$(CH_2)_p$—, $(C_1-C_6)$alkyl-(O=C)—O—$(C_1-C_6)$alkyl-, $(C_1-C_6)$alkyl-O—(=C)—O—$(C_1-C_6)$-alkyl-, $(C_1-C_6)$alkyl-(O=C)—O—, $(C_1-C_6)$alkyl-(O=C)—NH—$(CH_2)_p$—, H(O=C)—NH—$(CH_2)_p$—,

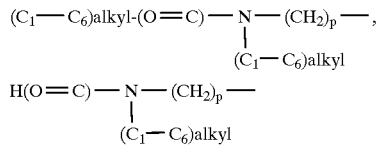

hydroxy, H—C(=O)—$(CH_2)_p$—, $(C_1-C_6)$alkyl-C(=O)—, $(C_1-C_6)$alkyl-O—C(=O)—, $R^4$—$(CH_2)_p$—O—C(=O)—, amino-$(CH_2)_p$—, hydroxy-$(C_1-C_6)$alkyl, $(C_1-C_6)$alkyl-O—$(C_1-C_6)$alkyl, —CHO and —CN;

$R^{11}$ is hydrogen or halo;

$R^{12}$ is hydrogen or halo;

$R^{13}$ is hydrogen, $(C_1-C_6)$alkyl, $(C_1-C_6)$alkyl-(C=O)—, $(C_1-C_6)$alkyl-O—(C=O)—, $(C_1-C_6)$alkyl-NH—(C=O)—, or di$(C_1-C_6)$alkyl-N—(C=O)—;

$R^{15}$ is hydrogen, —CN, $(C_1-C_6)$alkyl, halo, $CF_3$, —CHO or $(C_1-C_6)$alkoxy;

$R^{16}$ is hydrogen, —CN, $(C_1-C_6)$alkyl, halo, $CF_3$, —CHO or $(C_1-C_6)$alkoxy;

$R^{17}$ is hydrogen, —CN, $(C_1-C_6)$alkyl, halo, $CF_3$, CHO or $(C_1-C_6)$alkoxy;

n is an integer from zero to 3;

p is an integer from zero to 3;

wherein the dashed bond represents an optional double bond;

with the proviso that when $R^9$ is hydrogen, then one of $R^{11}$ and $R^{12}$ is other than hydrogen.

39. A method for treating a condition selected from cerebral deficits subsequent to cardiac bypass surgery and grafting, stroke, cerebral ischemia, spinal cord trauma, head trauma, Alzheimer's Disease, AIDS-induced dementia, migraine headaches, urinary incontinence, psychosis, perinatal hypoxia, hypoxia arrest, hypoglycemic neuronal damage, opiate tolerance, addiction withdrawal, ocular damage, retinopathy, retinal neuropathy, tinnitus, anxiety, emesis, brain edema, or chronic or acute pain in a mammal comprising administering to a mammal in need of such treatment an AMPA receptor antagonizing effective amount of a bicyclic compound or pharmaceutically acceptable salt of said bicyclic compound, of the formula

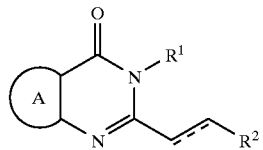

wherein ring A is a fused 5 membered heteroaromatic ring which, taken together with the carbon atoms common to both rings of the bicyclic system, has the formula

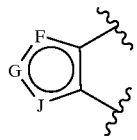

wherein one of said ring positions "F", "G" and "J" is selected from nitrogen, oxygen or sulfur, and the other two of said ring positions "F", "G", and "J" are carbons;

wherein said fused heteroaromatic rings may optionally be independently substituted on any of the carbon or nitrogen atoms capable of forming an additional bond with a substituent selected from hydrogen, $(C_1-C_6)$alkyl, halogen, trifluoromethyl, amino-$(CH_2)_n$—, $(C_1-C_6)$alkylamino-$(CH_2)_n$—, di$(C_1-C_6)$alkyl-amino-$(CH_2)_n$—, $(C_1-C_6)$alkoxy, hydroxy $(C_1-C_6)$alkyl, $(C_1-C_6)$alkyl-O—$(C_1-C_6)$alkyl-, —CN, $(C_1-C_6)$alkyl-CO—O—$(C_1-C_6)$alkyl-, $(C_1-C_6)$alkyl-O—CO—O—$(C_1-C_6)$alkyl, $(C_1-C_6)$alkyl-CO—O—, hydroxy, —$NO_2$, $R^3$—C(=O)—, $R^4$—O—C(=O)—, di$(C_1-C_6)$alkyl-N—C(=O)—, $(C_1-C_6)$cycloalkyl, and $R^4$—NH—C(=O)—, and phenyl optionally substituted with halo, $(C_1-C_6)$ alkyl, —CN, or —$CF_3$;

$R^1$ is substituted phenyl of the formula $Ph^1$ or heteroaryl wherein said heteroaryl is selected from the group consisting of pyridin-2-yl, pyridin-3-yl, pyridin-4-yl, wherein said heteroaryl may optionally be substituted on any of the atoms capable of forming an additional bond, up to a maximum of three substituents, with a substituent selected from hydrogen, $(C_1-C_6)$alkyl, halogen, trifluoromethyl, amino-$(CH_2)_n$—, $(C_1-C_6)$alkylamino-$(CH_2)_n$—, di$(C_1-C_6)$alkyl-amino-$(CH_2)_n$—, $(C_1-C_6)$alkoxy, hydroxy$(C_1-C_6)$alkyl, $(C_1-C_6)$alkyl-O—$(C_1-C_6)$alkyl-, —CN, $(C_1-C_6)$alkyl-CO—O—$(C_1-C_6)$alkyl-, $(C_1-C_6)$alkyl-O—CO—O—$(C_1-C_6)$alkyl, $(C_1-C_6)$alkyl-CO—O—, hydroxy, H—C(=O)—, $(C_1-C_6)$alkyl-C(=O)—, HO—C(=O)—, $(C_1-C_6)$alkyl-O—C(=O)—, $NH_2$—C(=O)—, $(C_1-C_6)$alkyl-NH—C(=O), and di$(C_1-C_6)$alkyl-NH—C(=O)—;

wherein said Ph¹ is a group of the formula

[structure: benzene ring with H at top, $R^8$ right-top, $R^7$ right-bottom, $R^6$ bottom, $R^5$ left-bottom, attachment point left-top]

$R^2$ is phenyl of the formula Ph² or a five or six membered heterocycle, wherein said six membered heterocycle has the formula

[structure: six-membered ring with N at top, $R^{14}$ at K position, $R^{15}$ at K-bottom, $R^{16}$ at L, $R^{17}$ at M]

wherein "N" is nitrogen; wherein said ring positions "K", "L" and "M" may be independently selected from carbon or nitrogen, with the proviso that only one of "K", "L" or "M" can be nitrogen;

wherein said five membered heterocycle has the formula

[structure: five-membered ring with T, P, Q positions, $R^{14}$, $R^{15}$, $R^{16}$ substituents]

wherein said ring positions "P," "Q" and "T" may be independently selected from carbon, nitrogen, oxygen or sulfur; with the proviso that only one of "P," "Q" or "T" can be oxygen or sulfur and at least one of "P," "Q" or "T" must be a heteroatom;

wherein said Ph² is a group of the formula

[structure: benzene ring with $R^{12}$ top, $R^{11}$ right-top, H right-bottom, $R^{10}$ bottom, $R^9$ left-bottom]

$R^3$ is hydrogen or $(C_1-C_6)$alkyl;

$R^4$ is hydrogen or $(C_1-C_6)$alkyl;

$R^5$ is hydrogen, $(C_1-C_6)$alkyl, halo, $CF_3$, $(C_1-C_6)$alkoxy or $(C_1-C_6)$alkylthiol;

$R^6$ is hydrogen or halo;

$R^7$ is hydrogen or halo;

$R^8$ is hydrogen or halo;

$R^9$ is hydrogen, $(C_1-C_6)$alkyl optionally substituted with one to three halogen atoms, halo, $CF_3$, $(C_1-C_6)$alkoxy optionally substituted with one to three halogen atoms, $(C_1-C_6)$alkylthiol, $R^{13}O—(CH_2)_p—$, $(C_1-C_6)$alkyl-NH—$(CH_2)_p—$, di$(C_1-C_6)$alkyl-N—$(CH_2)_p—$, $(C_1-C_5)$cycloalkyl-NH—$(CH_2)_p—$, $H_2N—(C=O)—(CH_2)_p—$, $(C_1-C_6)$alkyl-HN—$(C=O)—(CH_2)_p—$, di$(C_1-C_6)$alkyl-N—$(C=O)—(CH_2)_p—$, $(C_1-C_5)$cycloalkyl-NH—$(C=O)—(CH_2)_p—$, $R^{13}O—(C=O)—(CH_2)_p—$, $(C_1-C_6)$alkyl-$(O=C)—O—(C_1-C_6)$alkyl-, $(C_1-C_6)$alkyl-$O—(O=C)—O—(C_1-C_6)$-alkyl-, $(C_1-C_6)$alkyl-$(C_1-C_6)$alkyl-$(O=C)—N((C_1-C_6)alkyl)—(CH_2)_p—$, $H(O=C)—N((C_1-C_6)alkyl)—(CH_2)_p—$, hydroxy, $H—C(=O)—(CH_2)_p—$, $(C_1-C_6)$alkyl-$C(=O)—$, $(C_1-C_6)$alkyl-$O—$, $C(=O)—$, $R^4—(CH_2)_p—O—C(=O)—$, amino-$(CH_2)_p—$, hydroxy-$(C_1-C_6)$alkyl-, $(C_1-C_6)$alkyl-$O—(C_1-C_6)$alkyl-, and —CN;

$R^{10}$ and $R^{14}$ are hydrogen, $(C_1-C_6)$alkyl optionally substituted with one to three halogen atoms, halo, $CF_3$, $(C_1-C_6)$alkoxy optionally substituted with one to three halogen atoms, $(C_1-C_6)$alkylthiol, $R^{13}O—(CH_2)_p—$, $(C_1-C_6)$alkyl-NH—$(CH_2)_p—$, di$(C_1-C_6)$alkyl-N—$(CH_2)_p—$, $(C_1-C_5)$cycloalkyl-NH—$(CH_2)_p—$, $H_2N—(C=O)—$, $(CH_{2p}—$, $(C_1-C_6)$alkyl-HN—$(C=O)—(CH_2)_p—$, di$(C_1-C_6)$alkyl-N—$(C=O)—(CH_2)_p—$, $(C_1-C_6)$cycloalkyl-NH—$(C=O)—(CH_{2(p}—$, $R^{13}O—(C=O)—(CH_2)_p—$, $(C_1-C_6)$alkyl-$(O=C)—O—(C_1-C_6)$alkyl, $(C_1-C_6)$alkyl-$O—(O=C)—O—(C_1-C_6)$—alkyl-, $(C_1-C_6)$alkyl-$(O=C)—O—$, $(C_1-C_6)$alkyl-$(O=C)—NH—(CH_2)_p—$, alkyl-$(O=C)—N—(CH_2)_p—$, $H(O=C)—N—(CH_2)_p—$ $(C_1-C_6)$alkyl-$(O=C)—N((C_1-C_6)alkyl)—(CH_2)_p—$, $H(O=C)—N((C_1-C_6)alkyl)—(CH_2)_p—$, hydroxy, $H—C(=O)—(CH_2)_p—$, $(C_1-C_6)$alkyl-$C(=O)—$, $(C_1-C_6)$alkyl-$O—C(=O)—$, $R^4—(CH_2)_p—O—C(=O)—$, amino-$(CH_2)_p—$, hydroxy-$(C_1-C_6)$alkyl, $(C_1-C_6)$alkyl-$O—(C_1-C_6)$alkyl, —CHO and —CN;

$R^{11}$ is hydrogen or halo;

$R^{12}$ is hydrogen or halo;

$R^{13}$ is hydrogen, $(C_1-C_6)$alkyl, $(C_1-C_6)$alkyl-$(C=O)—$, $(C_1-C_6)$alkyl-$O—(C=O)—$, $(C_1-C_6)$alkyl-NH—$(C=O—$, or di$(C_1-C_6)$alkly-N—$(C=O)—$;

$R^{15}$ is hydrogen —CN, $(C_1-C_6)$alkyl, halo, $CF_3$, —CHO or $(C_1-C_6)$alkoxy;

$R^{16}$ is hydrogen, —CN, $(C_1-C_6)$alkyl, halo, $CF_3$, —CHO or $(C_1-C_6)$alkoxy;

$R^{17}$ is hydrogen, —CN, $(C_1-C_6)$alkyl, halo, $CF_3$, CHO or $(C_1-C_6)$alkoxy;

n is an integer from zero to 3;

p is an integer from zero to 3;

wherein the dashed bond represents an optional double bond;

with the proviso that when $R^9$ is hydrogen, then one of $R^{11}$ and $R^{12}$ is other than hydrogen.

40. A method for treating disorders the treatment of which is facilitated by enhanced glutamate neurotransmission in a mammal, comprising administering to a mammal requiring such treatment an AMPA receptor antagonizing effective amount of a bicyclic compound, or pharmaceutically acceptable salt of said bicyclic compound, of the formula

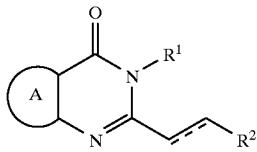

wherein ring A is a fused 5 membered heteroaromatic ring which, taken together with the carbon atoms common to both rings of the bicyclic system, has the formula

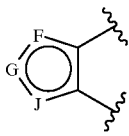

wherein one of said ring positions "F", "G" and "J" is selected from nitrogen, oxygen or sulfur, and the other two of said ring positions "F", "G", and "J" are carbons;

wherein said fused heteroaromatic rings may optionally be independently substituted on any of the carbon or nitrogen atoms capable of forming an additional bond with a substituent selected from hydrogen, $(C_1-C_6)$ alkyl, halogen, trifluoromethyl, amino-$(CH_2)_n$—, $(C_1-C_6)$alkylamino-$(CH_2)_n$—, di$(C_1-C_6)$alkyl-amino-$(CH_2)_n$—, $(C_1-C_6)$alkoxy, hydroxy $(C_1-C_6)$alkyl, $(C_1-C_6)$alkyl-O—$(C_1-C_6)$alkyl-, —CN, $(C_1-C_6)$alkyl-CO—O—$(C_1-C_6)$alkyl-, $(C_1-C_6)$alkyl-O—CO—O—$(C_1-C_6)$alkyl, $(C_1-C_6)$alkyl-CO—O—, hydroxy, —NO$_2$, $R^3$—C(=O)—, $R^4$—O—C(=C)—, di$(C_1-C_6)$alkyl-N—C(=O)—, $(C_1-C_6)$cycloalkyl, and $R^4$—NH—C(=O)—, and phenyl optionally substituted with halo, $(C_1-C_6)$alkyl, —CN, or —CF$_3$;

$R^1$ is substituted phenyl of the formula Ph$^1$ or heteroaryl wherein said heteroaryl is selected from the group consisting of pyridin-2-yl, pyridin-3-yl, pyridin-4-yl, wherein said heteroaryl may optionally be substituted on any of the atoms capable of forming an additional bond, up to a maximum of three substituents, with a substituent selected from hydrogen, $(C_1-C_6)$alkyl, halogen, trifluoromethyl, amino-$(CH_2)_n$—, $(C_1-C_6)$ alkyl-amino-$(CH_2)_n$—, di$(C_1-C_6)$alkyl-amino-$(C_2)_n$—, $C_1-C_6$)alkoxy, hydroxy$(C_1-C_6)$alkyl, $(C_1-C_6)$alkyl-O—$(C_1-C_6)$alkyl-, —CN, $(C_1-C_6)$alkyl—CO—O—$(C_1-C_6)$alkyl-, $(C_1-C_6)$alkyl-O—CO—O—$(C_1-C_6)$alkyl, $(C_1-C_6)$alkyl-CO—O—, hydroxy, H—C(=O)—, $(C_1-C_6)$alkyl-C(=O)—, HO—C(=O)—, $(C_1-C_6)$alkyl-O—C(=O)—, NH$_2$—C(=O)—, $(C_1-C_6)$alkyl-NH—C(=O), and di$(C_1-C_6)$alkyl-NH—C(=O)—;

wherein said Ph$^1$ is a group of the formula

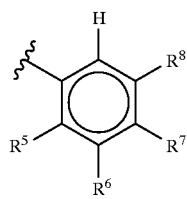

$R^2$ is phenyl of the formula Ph$^2$ or a five or six membered heterocycle, wherein said six membered heterocycle has the formula

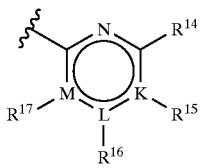

wherein "N" is nitrogen; wherein said ring positions "K", "L" and "M" may be independently selected from carbon or nitrogen, with the proviso that only one of "K", "L" or "M" can be nitrogen;

wherein said five membered heterocycle has the formula

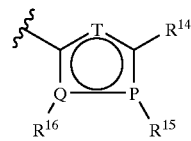

wherein said ring positions "P," "Q" and "T" may be independently selected from carbon, nitrogen, oxygen or sulfur; with the proviso that only one of "P," "Q" or "T" must be a heteroatom;

wherein said Ph$^2$ is a group of the formula

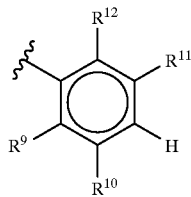

$R^3$ is hydrogen or $(C_1-C_6)$ alkyl;
$R^4$ is hydrogen or $(C_1-C_6)$ alkyl;
$R^5$ is hydrogen, $(C_1-C_6)$alkyl, halo, CF$_3$, $(C_1-C_6)$alkoxy or $(C_1-C_6)$alkylthiol;
$R^6$ is hydrogen or halo;
$R^7$ is hydrogen or halo;
$R^8$ is hydrogen or halo;
$R^9$ is hydrogen, $(C_1-C_6)$alkyl optionally substituted with one to three halogen atoms, halo, CF$_3$, $(C_1-C_6)$alkoxy optionally substituted with one to three halogen atoms, $(C_1-C_6)$alkylthiol, $R^{13}$O—$(CH_2)_p$—, $(C_1-C_6)$alkyl-NH—$(CH_2)_p$—, di$(C_1-C_6)$alkyl-N—$(CH_2)_p$—, $(C_1-C_5)$cycloalkyl-NH—$(CH_2)_p$—, H$_2$N—(C=O)—

$(CH_2)_p$—, $(C_1-C_6)$alkyl-HN—(C=O)—$(CH_2)_p$—, di$(C_1-C_6)$alkyl-N—(C=O)—$(CH_2)_p$—, $(C_1-C_5)$)cycloalkyl-NH—(C=O)—$(CH_2)_p$—, $R^{13}$O—(C=O)—$(CH_2)_p$—, $(C_1-C_6)$alkyl-(O=C)—O—$(C_1-C_6)$alkyl-, $(C_1-C_6)$alkyl-O—(O=C)—O—$(C_1-C_6)$-alkyl-, $(C_1-C_6)$alkyl-$(C_1-C_6)$alkyl-(O=C)—N($(C_1-C_6)$alkyl)—$(CH_2)_p$—, H(O=C)—N($(C_1-C_6)$alkyl)—$(CH_2)_p$—, hydroxy, H—C(=O)—$(CH_2)_p$—, $(C_1-C_6)$alkyl-C(=O)—, $(C_1-C_6)$alkyl-O—C(=O)—, $R^4$—$(CH_2)_p$—O—C(=O)—, amino-$(CH_2)_p$—, hydroxy-$(C_1-C_6)$alkyl-, $(C_1-C_6)$alkyl-O—$(C_1-C_6)$alkyl-, and —CN;

$R^{10}$ and $R^{14}$ are hydrogen, $(C_1-C_6)$alkyl optionally substituted with one to three halogen atoms, halo, $CF_3$, $(C_1-C_6)$alkoxy optionally substituted with one to three halogen atoms, $(C_1-C_6)$alkylthiol, $R^{13}$—$(CH_2)_p$—, $(C_1-C_6)$alkyl-NH—$(CH_2)_p$—, di$(C_1-C_6)$alkyl-N—$(CH_2)_p$—, $(C_1-C_5)$cycloalkyl-NH—$(CH_2)_p$—, $H_2N$—(C=O)—$(CH_2)_p$—, $(C_1-C_6)$alkyl-HN—(C=O)—$(CH_2)_p$—, di$(C_1-C_6)$alkyl-N—(C=O)—$(CH_2)_p$—, $(C_1-C_5)$cycloalkyl-NH—(C=O)—$(CH_2)_p$—, $R^{13}$O—(C=O)—$(CH_2)_p$—, $(C_1-C_6)$alkyl-(O=C)—O—$(C_1-C_6)$alkyl-, $(C_1-C_6)$alkyl-O—(O=C)—O—$(C_1-C_6)$-alkyl-, $(C_1-C_6)$alkyl-(O=C)—O—, $(C_1-C_6)$alkyl-(O=C)—NH—$(CH_2)_p$—, H(O=C)—NH—$(CH_2)_p$—, $(C_1-C_6)$alkyl-(O=C)—N($(C_1-C_6)$alkyl)—$(CH_2)_p$—, H(O=C)—N($(C_1-C_6)$alkyl)—$(CH_2)_p$—, hydroxy, H—C(=O)—$(CH_2)_p$—, $(C_1-C_6)$alkyl-C(=O)—, $(C_1-C_6)$alkyl-O—C(=O)—, $R^4$—$(CH_2)_p$—O—C(=O)—, amino-$(CH_2)_p$—, hydroxy-$(C_1-C_6)$alkyl, $(C_1-C_6)$alkyl-O—$(C_1-C_6)$alkyl, —CHO and —CN, $R^{11}$ is hydrogen or halo;

$R^{12}$ is hydrogen or halo;

$R^{13}$ is hydrogen, $(C_1-C_6)$alkyl, $(C_1-C_6)$alkyl-(C—O)—, $(C_1-C_6)$alkyl-O—(C=O)—, $(C_1-C_6)$alkyl-NH—(C=C)—, or di$(C_1-C_6)$alkyl-N—(C=O)—;

$R^{15}$ is hydrogen, —CN, $(C_1-C_6)$alkyl, halo, $CF_3$, —CHO or $(C_1-C_6)$alkoxy;

$R^{16}$ is hydrogen, —CN, $(C_1-C_6)$alkyl, halo, $CF_3$, —CHO or $(C_1-C_6)$alkoxy;

$R^{17}$ is hydrogen, —CN, $(C_1-C_6)$alkyl, halo, $CF_3$, CHO or $(C_1-C_6)$alkoxy;

n is an integer from zero to 3;

p is an integer from zero to 3;

wherein the dashed bond represents an optional double bond;

with the proviso that when $R^9$ is hydrogen, then one of $R^{11}$ and $R^{12}$ is other than hydrogen.

* * * * *